US011351269B2

(12) United States Patent
Lewis et al.

(10) Patent No.: US 11,351,269 B2
(45) Date of Patent: Jun. 7, 2022

(54) ANTI-NTB-A ANTIBODIES AND RELATED COMPOSITIONS AND METHODS

(71) Applicant: SEAGEN INC., Bothell, WA (US)

(72) Inventors: Timothy Lewis, Kenmore, WA (US); Lori Westendorf, Snohomish, WA (US); Django Sussman, Seattle, WA (US); Che-Leung Law, Shoreline, WA (US)

(73) Assignee: Seagen Inc., Bothell, WA (US)

( * ) Notice: Subject to any disclaimer, the term of this patent is extended or adjusted under 35 U.S.C. 154(b) by 559 days.

(21) Appl. No.: 15/739,363

(22) PCT Filed: Jun. 30, 2016

(86) PCT No.: PCT/US2016/040307
§ 371 (c)(1),
(2) Date: Dec. 22, 2017

(87) PCT Pub. No.: WO2017/004330
PCT Pub. Date: Jan. 5, 2017

(65) Prior Publication Data
US 2018/0169257 A1  Jun. 21, 2018

Related U.S. Application Data

(60) Provisional application No. 62/321,849, filed on Apr. 13, 2016, provisional application No. 62/186,596, filed on Jun. 30, 2015.

(51) Int. Cl.
| | |
|---|---|
| A61K 47/68 | (2017.01) |
| C07K 16/28 | (2006.01) |
| A61K 47/65 | (2017.01) |
| A61P 35/00 | (2006.01) |
| A61K 39/00 | (2006.01) |

(52) U.S. Cl.
CPC .......... *A61K 47/6803* (2017.08); *A61K 47/65* (2017.08); *A61K 47/6811* (2017.08); *A61K 47/6851* (2017.08); *A61P 35/00* (2018.01); *C07K 16/2803* (2013.01); *A61K 2039/505* (2013.01); *A61K 2039/572* (2013.01); *A61K 2121/00* (2013.01); *C07K 2317/24* (2013.01); *C07K 2317/33* (2013.01); *C07K 2317/567* (2013.01); *C07K 2317/73* (2013.01); *C07K 2317/732* (2013.01); *C07K 2317/92* (2013.01)

(58) Field of Classification Search
CPC . A61K 47/6803; A61K 47/6851; A61P 35/00; A61P 35/02; C07K 16/2803; C07K 2317/565; C07K 2317/24; C07K 2317/56
See application file for complete search history.

(56) References Cited

U.S. PATENT DOCUMENTS

| | | | | |
|---|---|---|---|---|
| 7,960,516 B2 * | 6/2011 | Matheus | ............ | C07K 16/2863 530/387.3 |
| 2009/0142261 A1 * | 6/2009 | Hsu | ......... | A61P 43/00 424/1.49 |

FOREIGN PATENT DOCUMENTS

| | | | |
|---|---|---|---|
| CA | 2905597 A1 | 9/2014 | |
| WO | WO2008/027739 A2 | 3/2008 | |
| WO | WO2008/027739 A3 | 3/2008 | |
| WO | WO2013/173493 A2 | 11/2013 | |
| WO | WO 2013/173493 A3 | 11/2013 | |
| WO | WO2013/173496 A2 | 11/2013 | |
| WO | WO2013/173496 A3 | 11/2013 | |
| WO | WO2014/057119 A1 | 4/2014 | |
| WO | WO2014/100740 A1 | 6/2014 | |
| WO | WO2014/100740 A1 | 6/2014 | |
| WO | WO2015/095002 A1 | 6/2015 | |
| WO | WO-2016039402 A1 * | 3/2016 | ............. C07K 16/40 |
| WO | WO2017/004330 A1 | 1/2017 | |
| WO | WO2017/160954 A1 | 9/2017 | |

OTHER PUBLICATIONS

Tiberghien et al, Medicinal Chemistry Letters, 2016, vol. 7, pp. 983-987 (Year: 2016).*
Gertz and Rajkumar, Current Treatment Options in Oncology, 2002, vol. 3, pp. 261-271 (Year: 2002).*
Ngendahayo et al, International Journal of Surgical Pathology, 2012, vol. 21, pp. 177-180 (Year: 2012).*
Brinkmann and Kontermann (mAbs, 2017, vol. 9, pp. 182-212) (Year: 2017).*
Leelawattanachal et al, PLOS one, 2015, vol. 10, No. 4, e0124440 (Year: 2015).*
Schier et al, Journal of Molecular Biology, 1996, vol. 255, pp. 28-43 (Year: 1996).*
Doerner et al (FEBS Letters, 2014, vol. 588, pp. 278-287) (Year: 2014).*
PCT Application No. PCT/US2016/040307, Search Report and Written Opinion dated Sep. 30, 2016, 14 pages.
Bottino, et al., "NTB-A, a Novel SH2D1A-associated Surface Molecule Contributing to the Inability of Natural Killer Cells to Kill Epstein-Barr Virus-infected B Cells in X-linked Lymphoproliferative Disease", J. Exp. Med., vol. 194, No. 3, pp. 235-246, (Aug. 2001).
Korver, et al., "The lymphoid cell surface receptor NTB-A: a novel monoclonal antibody target for leukaemia and lymphoma therapeutics", British Journal of Haematology, 137, pp. 307-318, (2007).

(Continued)

*Primary Examiner* — Karen A. Canella
(74) *Attorney, Agent, or Firm* — Seagen Inc.

(57) ABSTRACT

Disclosed are antibodies, including antibody drug conjugates, that specifically bind to NTB-A. Also disclosed are methods for using the anti-NTB-A antibodies to detect or modulate activity of (e.g., inhibit proliferation of) an NTB-A-expressing cell, as well as for diagnoses or treatment of diseases or disorders (e.g., cancer) associated with NTB-A-expressing cells, such as multiple myeloma, non-Hodgkin lymphoma and acute myeloid leukemia.

90 Claims, 7 Drawing Sheets
Specification includes a Sequence Listing.

(56) References Cited

OTHER PUBLICATIONS

Valdez, et al., "NTB-A, a New Activating Receptor in T Cells That Regulates Autoimmune Disease", The Journal of Biological Chemistry, vol. 279, No. 18, pp. 18662-18669, (2004).
EP Patent Application No. 16818762.3, Supplementary European Search Report dated Nov. 29, 2018, 4 pages.
Jeffrey, et al., "A Potent Anti-CD70 Antibody-Drug Conjugate Combining a Dimeric Pyrrolobenzodiazepine Drug with Site-Specific Conjugation Technology", Bioconjugate Chemistry, 24, 1256-1263, (2013).

* cited by examiner

```
                 ....|....|....|....|....|....|....|....|....|....|....|....|....|....|
                          10         20         30         40         50         60         70
20F3 VH          ....I....P.........ET.I......K..KD.K......K................MINTYSGEPRYADDFK.R.VE..A..
20F3 huFW        QVQLVQSGSELKKPGASVKVSCKASGYTFTMYGMNWVRQAPGQGLEWMGWINTYSGEPRYADDFKGRFVF
20F3 HA          ..................................................................
20F3 HB          .......I..........................................................
20F3 HC          .......I.........................D.................................
20F3 HD          .......I........................D.K.................................
20F3 HE          .......I........................D.K.................................

....|....|....|....|....|....|....|....|....|....|....|....|
                          80         90        100        110
20F3 VH          ...EK.AM....WN..K..M.T.F.............CARDYGRWYFDVWGQGTTVTVSS.....T..........
20F3 huFW        SLDTSVSTAYLQISSLKAEDTAVYYCARDYGRWYFDVWGQGTTVTVSS
20F3 HA          ............................................
20F3 HB          ....K.......................................
20F3 HC          ....K..W.....................................
20F3 HD          ....K..W.....................................
20F3 HE          ....K..W.................................F...
```

20F3 VH                  SEQ ID NO:3
20F3 huFW                SEQ ID NO:4
20F3 HA                  SEQ ID NO:5
20F3 HB                  SEQ ID NO:6
20F3 HC                  SEQ ID NO:7
20F3 HD                  SEQ ID NO:8
20F3 HE                  SEQ ID NO:9

20F3 vH huFW: vH7-4-1/JH6

*Fig. 1*

```
              .    :    .    :    .    :    .    :    .    :    .    :    .    :
              5         10        20        30        40        50        60        70
20F3 VL       .....Q...S...L..A...KV.MT......SS.KFW..........V..........SY
20F3 huFW     EIVLTQSPATLSLSPGERATLSC RASSVSYMH WYQQKPGQAPRLLIY ATSNLES GIPARFSGSGSGTDF
20F3 LA       .................................................................Y
20F3 LB       ...Q..S.................M....................FW.................Y
20F3 LC       ...Q..S......................................FW.................Y
20F3 LD       ...Q..S......................................FW..V..............Y

.    :    .    :    .    :    .    :
              80        90        100       L....
20F3 VL       S...RV..A..A.T............L....         SEQ ID NO:13
20F3 huFW     TLTISSLEPEDFAVYYC QQWSSTPRT FGQGTKVEIKR   SEQ ID NO:14
20F3 LA       ............................             SEQ ID NO:15
20F3 LB       ............................             SEQ ID NO:16
20F3 LC       ....S.......................             SEQ ID NO:17
20F3 LD       ....S.......................             SEQ ID NO:18
```

20F3 vL huFW: vK3-11/JK4

*Fig. 2*

ANTI-NTB-A ANTIBODIES AND RELATED COMPOSITIONS AND METHODS

CROSS REFERENCE TO RELATED APPLICATIONS

This application is a U.S. national stage filing under 35 U.S.C. 371 of International Application No. PCT/US2016/040307, filed Jun. 30, 2016, which claims the benefit of U.S. Provisional Patent Application No. 62/186,596, filed Jun. 30, 2015 and U.S. Provisional Patent Application No. 62/321,849, filed Apr. 13, 2016, both of which are incorporated herein by reference in their entirety.

REFERENCE TO A SEQUENCE LISTING

This application includes an electronic sequence listing in a file named NTBA-00313US_Sequence_Listing_ST25.txt, created on Nov. 15, 2017 and containing 29 KB, which is hereby incorporated by reference.

BACKGROUND

NTB-A, a single-pass type I membrane glycoprotein also referred to as SLAMF6, is an immunoglobulin superfamily (Ig-SF) member belonging to the CD2/SLAM subfamily. See, e.g., Bottino et al., *J. Exp. Med.* 194:235-246, 2001. NTB-A is characterized, in its extracellular portion, by an N-terminal V-type domain followed by a C2-type domain, while the intracytoplasmic portion contains three tyrosine-based motifs: two immunoreceptor tyrosine-based switch motifs (ITSM; TxYxxV/I) and a classical immunoreceptor tyrosine-based inhibition motif (ITIM; I/V/L/SxYxxL). See id. Through its ITSM motifs, NTB-A associates with the SH2 domain of the SLAM-associated protein SH2D1A and the related Ewing's sarcoma activated transcript (EAT) 2. See Bottino et al., supra; Falco et al., *Eur. J. Immunol.* 34:1663-1672, 2004; Flaig et al., *J. Immunol.* 172:6524-6527, 2004.

NTB-A is expressed on natural killer (NK) cells, NK-like T-cells, T-cells, monocytes, dendritic cells, B-cells, and eosinophils. See Salort J D. et al., *Immunology Letters* 129-136, 2011; Matesanz-Isabel et al., *Immunology Letters* 104-112, 2011; Munitz et al., *Journal of Immunology* 174:110-118, 2005; Bottino et al., *Journal of Experimental Medicine* 194(3):235-246; 2001. NTB-A can function through homotypic interactions (i.e., as a self-ligand), and has been shown to act as a positive regulator of NK cell functions via signaling, inducing NK cell cytotoxicity. See, e.g., See Bottino et al., supra; Falco et al., supra; Flaig et al., supra. NTB-A has also been shown to be expressed on B-cells from chronic lymphocytic leukemia (CLL) and B-cell lymphoma patients. See Korver et al., *British Journal of Haematology* 137:307-318, 2007.

BRIEF DESCRIPTION OF THE FIGURES

FIG. 1 shows a sequence alignment of the mouse 20F3 heavy chain variable region, the humanized sequence with mouse CDRs (boxed) in a human acceptor without back-mutations, and humanized variants, HA-HE. CDRs are as defined by Kabat.

FIG. 2 shows a sequence alignment of the mouse 20F3 light chain variable region, the humanized sequence with mouse CDRs (boxed) in a human acceptor without back-mutations and humanized variants, LA-LD. CDRs are as defined by Kabat.

DEFINITIONS

Figure 3:
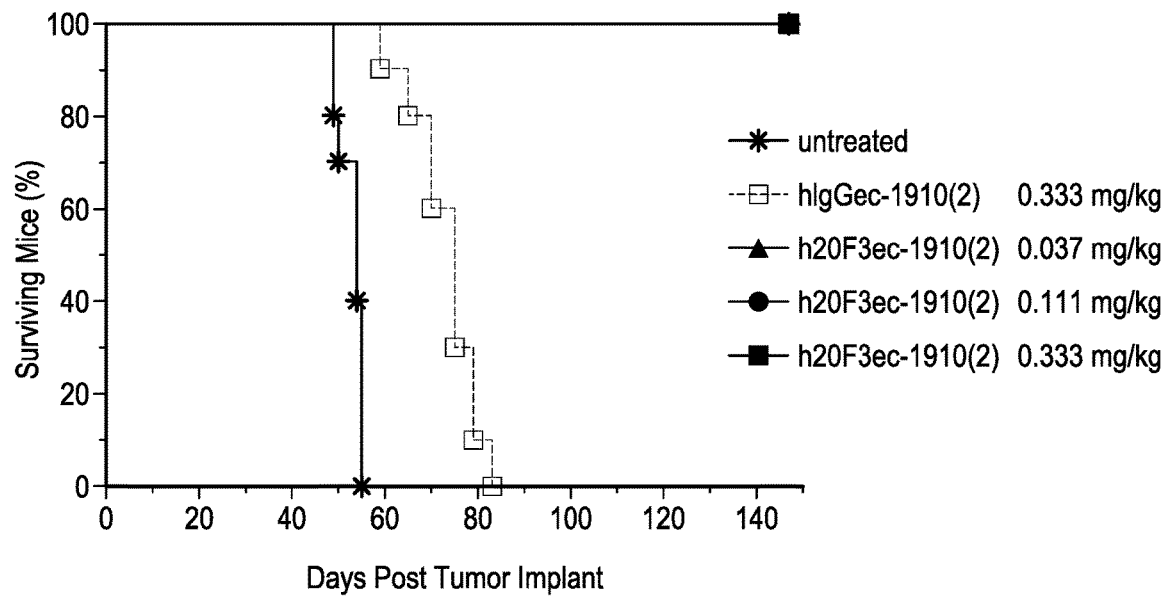
FIG. 3 shows the results of a multiple myeloma disseminated xenograft study in the MM.1R cell line in NSG mice. The dose is indicated on the figure. The ADC is a humanized 20F3 PBD antibody drug conjugate

An "antibody-drug conjugate" refers to an antibody conjugated to a cytotoxic agent or cytostatic agent. Typically, antibody-drug conjugates bind to a target antigen (e.g., NTB-A) on a cell surface followed by internalization of the antibody-drug conjugate into the cell and release of the drug.

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" denotes immunoglobulin proteins produced by the body in response to the presence of an antigen and that bind to the antigen, as well as antigen-binding fragments and engineered variants thereof. Hence, the term "antibody" includes, for example, intact monoclonal antibodies (e.g., antibodies produced using hybridoma technology) and antigen-binding antibody fragments, such as F(ab')$_2$ and Fab fragments. Genetically engineered intact antibodies and fragments, such as chimeric antibodies, humanized antibodies, single-chain Fv fragments, single-chain antibodies, diabodies, minibodies, linear antibodies, multivalent or multispecific (e.g., bispecific) hybrid antibodies, and the like are also included. Thus, the term "antibody" is used expansively to include any protein that comprises an antigen-binding site of an antibody and is capable of specifically binding to its antigen. The term "antibody" also includes an antibody by itself ("naked antibody") or an antibody conjugated to a cytostatic or cytotoxic drug.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region are, in general, made to improve or alter characteristics such as, e.g., complement fixation, interaction with cells, and other effector functions. Typically, changes in the variable region are made to improve the antigen-binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). Commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450: 23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')$_2$, F(ab)c, diabodies, minibodies, nanobodies, Fab-scFv fusions, bispecific (scFv)$_4$-IgG, and bispecific (scFv)$_2$-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

The term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 kDa or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 kDa or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. Thus, the term "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each variable region domain is in accordance with the definitions of Kabat, *Sequences of Proteins of Immunological Interest* (National Institutes of Health, Bethesda, Md., 1987 and 1991). Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3. If so noted, the assignment of CDRs can be in accordance with IMGT® (Lefranc et al., *Developmental & Comparative Immunology* 27:55-77; 2003) in lieu of Kabat.

Unless the context dictates otherwise, the term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. The antibodies described herein are monoclonal antibodies.

The term "humanized VH domain" or "humanized VL domain" refers to an immunoglobulin VH or VL domain comprising some or all CDRs entirely or substantially from a non-human donor immunoglobulin (e.g., a mouse or rat) and variable domain framework sequences entirely or substantially from human immunoglobulin sequences. The non-human immunoglobulin providing the CDRs is called the "donor" and the human immunoglobulin providing the framework is called the "acceptor." In some instances, humanized antibodies will retain some non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat (or IMGT)) are identical between the respective CDRs. In particular variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions (preferably conservative substitutions) across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least about 80%, at least 85%, at least 90%, at least 95%, or 100% of corresponding residues defined by Kabat are identical. Hence, all parts of a humanized antibody, except the CDRs, are entirely or substantially from corresponding parts of natural human immunoglobulin sequences.

Antibodies are typically provided in isolated form. This means that an antibody is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies are at least 60%, 70%, 80%, 90%, 95 or 99% w/w pure of interfering proteins and contaminants from production or purification. Antibodies, including isolated antibodies, can be conjugated to cytotoxic agents and provided as antibody drug conjugates.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols, in Methods in Molecular Biology*, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other (provided that such mutations do not produce a global alteration in antigen structure). Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody inhibits binding of the reference antibody. Competition is assessed according to the format provided in the examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Antibodies identified by competition assay also include those that indirectly compete with a reference antibody by causing a conformational change in the target protein thereby preventing binding of the reference antibody to a different epitope than that bound by the test antibody.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit may further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector may also include additional nucleic acid segments such as, for example, one or more origins of replication or one or more selectable markers. Expression vectors are generally derived from plasmid or viral DNA, or may contain elements of both.

In antibodies or other proteins described herein, reference to amino acid residues corresponding to those specified by SEQ ID NO includes post-translational modifications of such residues.

The term "patient" includes human and other mammalian subjects that receive either prophylactic or therapeutic treatment.

The term "effective amount," in the context of treatment of a NTB-A-expressing disorder by administration of an anti-NTB-A antibody as described herein, refers to an amount of such antibody that is sufficient to inhibit the occurrence or ameliorate one or more symptoms of the NTB-A-expressing disorder. An effective amount of an antibody is administered in an "effective regimen." The term "effective regimen" refers to a combination of amount of the antibody being administered and dosage frequency adequate to accomplish prophylactic or therapeutic treatment of the disorder.

For purposes of classifying amino acids substitutions as conservative or nonconservative, the following amino acid substitutions are considered conservative substitutions: serine substituted by threonine, alanine, or asparagine; threonine substituted by proline or serine; asparagine substituted by aspartic acid, histidine, or serine; aspartic acid substituted by glutamic acid or asparagine; glutamic acid substituted by glutamine, lysine, or aspartic acid; glutamine substituted by arginine, lysine, or glutamic acid; histidine substituted by tyrosine or asparagine; arginine substituted by lysine or glutamine; methionine substituted by isoleucine, leucine or valine; isoleucine substituted by leucine, valine, or methionine; leucine substituted by valine, isoleucine, or methionine; phenylalanine substituted by tyrosine or tryptophan; tyrosine substituted by tryptophan, histidine, or phenylalanine; proline substituted by threonine; alanine substituted by serine; lysine substituted by glutamic acid, glutamine, or arginine; valine substituted by methionine, isoleucine, or leucine; and tryptophan substituted by phenylalanine or tyrosine. Conservative substitutions can also mean substitutions between amino acids in the same class. Classes are as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc region of an Ig. Such functions can be, for example, antibody-dependent cellular cytotoxicity, antibody-dependent cellular phagocytosis, or complement-dependent cytotoxicity. Such function can be effected by, for example, binding of an Fc region to an Fc receptor on an immune cell with phagocytic or lytic activity or by binding of an Fc region to components of the complement system. Typically, the effect(s) mediated by the Fc-binding cells or complement components result in inhibition and/or depletion of the NTB-A-targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by $CD16^+$ effector cells through the secretion of membrane pore-forming proteins and proteases, while phagocytosis is mediated by $CD32^+$ and $CD64^+$ effector cells (see *Fundamental Immunology*, 4th ed., Paul ed., Lippincott-Raven, N.Y., 1997, Chapters 3, 17 and 30; Uchida et al., *J. Exp. Med.* 199:1659-69, 2004; Akewanlop et al., *Cancer Res.* 61:4061-65, 2001; Watanabe et al., *Breast Cancer Res. Treat.* 53:199-207, 1999). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N.Y., 2005, Chapter 2).

The term "antibody-dependent cellular cytotoxicity," or "ADCC," is a mechanism for inducing cell death that depends on the interaction of antibody-coated target cells with immune cells possessing lytic activity (also referred to as effector cells). Such effector cells include natural killer cells, monocytes/macrophages and neutrophils. The effector cells attach to an Fc region of Ig bound to target cells via their antigen-combining sites. Death of the antibody-coated target cell occurs as a result of effector cell activity.

The term "antibody-dependent cellular phagocytosis," or "ADCP," refers to the process by which antibody-coated cells are internalized, either in whole or in part, by phagocytic immune cells (e.g., macrophages, neutrophils and dendritic cells) that bind to an Fc region of Ig.

The term "complement-dependent cytotoxicity," or "CDC," refers to a mechanism for inducing cell death in which an Fc region of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-NTB-A antibody is formulated.

The phrase "pharmaceutically acceptable salt," refers to pharmaceutically acceptable organic or inorganic salts. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, when a value is expressed as "about" X or "approximately" X, the stated value of X will be understood to be accurate to ±10%.

Glycosylation depends on the host cell used to express the antibody. Because the cell type used for expression of recombinant antibodies as potential therapeutics is rarely the native cell, significant variations in the glycosylation pattern of the antibodies can occur between recombinantly expressed antibodies in nonnative cells and antibodies of the same primary heavy and light chain sequences expressed in their native cells. Mammalian cell lines of rodent origin (such as SP2/0, CHO or BHK) are able to confer a glycosylation that has some similarity to a human glycosylation. However, some human components may be missing (such as the 2,6-linked sialylation) and a number of other components not usually found in humans may be present, such as terminals sialic acids that do not usually exist in human cells (NeuGc, for example) or terminal galactose linked to another galactose in a way that is usually absent from human cells (Gal-Gal structures). Recombinant-IgGs expressed in CHO cells are generally less galactosylated compared to the recombinant immunoglobulins expressed in mouse myeloma cells. Accordingly, recombinant IgGs produced in CHO cells may contain higher levels of G0 glycans compared with rIgGs produced in mouse myeloma cell lines.

The glycosylation structure of antibodies can be analyzed by conventional techniques of carbohydrate analysis, including lectin chromatography, NMR, Mass spectrometry, HPLC, gel permeation chromatography, monosaccharide compositional analysis, sequential enzymatic digestion, and High-Performance Anion-Exchange Chromatography with Pulsed Amperometric Detection, which uses high pH anion exchange chromatography to separate oligosaccharides based on charge. Methods for releasing oligosaccharides for analytical purposes include enzymatic treatment (commonly performed using peptide-N-glycosidase F/endo-beta-galactosidase), elimination using harsh alkaline environment to release mainly O-linked structures, and chemical methods using anhydrous hydrazine to release both N- and O-linked oligosaccharides.

Thus, the glycosylation pattern of a recombinantly expressed antibody can be characteristic of the cell type in which expression is performed (e.g., CHO) and distinguishable different by any of the above techniques from other cell types particularly cells of other species, such as mouse and human.

Solvates in the context of the invention are those forms of the compounds of the invention that form a complex in the solid or liquid state through coordination with solvent molecules. Hydrates are one specific form of solvates, in which the coordination takes place with water. Preferred solvates in the context of the present invention are hydrates.

DETAILED DESCRIPTION

I. General

The invention provides, inter alia, 20F3 antibodies that specifically bind to NTB-A, as well as chimeric, veneered and humanized forms thereof. Also provided are antibodies that compete for binding with the 20F3 antibodies or bind to the same epitope as the 20F3 antibody. The antibodies are useful, e.g., for treatment and diagnoses of various NTB-A-expressing cancers, as well as for detecting NTB-A (e.g., detection of NTB-A expression on cells). Methods for such treatment, diagnoses, and NTB-A detection using antibodies of the invention, including naked antibodies and conjugated antibodies are also provided.

II. Target Molecules

Unless otherwise indicated, NTB-A means a human NTB-A. An exemplary human sequence is assigned SEQ ID NO:1 (Swiss Prot Q96DU3). Four splice-variant isoforms are known. The mature extracellular region is bounded by residues 22-226 of Q96DU3. A shorter extracellular domain in isoform 4 has the C2 domain and two ITSM motifs, and lacks residues 18-121, which include the immunoglobulin domain.

Unless otherwise apparent from the context, reference to NTB-A means at least an extracellular domain of the protein according to the complete protein other than a cleavable signal peptide (amino acids 1-21 of Q96DU3).

Cynomolgus NTB-A (SEQ ID NO:2) (cyno-NTB-A) has 84.6% amino acid identity and 93.3% amino acid similarity with human NTB-A (SEQ ID NO:1).

III. Antibodies

A. Binding Specificity and Functional Properties

The disclosure refers inter alia to the mouse antibody designated 20F3, and chimeric, veneered and humanized forms of the 20F3 antibody as well as antibodies that compete with the 20F3 antibody for binding to NTB-A and antibodies that bind to the same epitope as the 20F3 antibody. The 20F3 antibody binds to the canonical form of human NTB-A (SEQ ID NO:1), human isoform 4 and to cynomolgus monkey NTB-A. These binding characteristics suggest its epitope lies outside the segment of NTB-A absent in isoform 4 (within residues 128-226) and at an epitope that it entirely or substantially conserved between human and cynomolgus forms of NTB-A.

The humanized HDLD 20F3 antibody has a Kd for human NTB-A isoform-1 on Ramos cells of about 2 nM. Other humanized forms of the 20F3 antibody preferably have a Kd substantially the same or within a factor of 2, 3 or 5 fold that of the HDLD 20F3 antibody. The humanized HDLD antibody has an EC50 for human NTB-A on Ramos cells of about 12 nM in an antigen binding competition assay. Some humanized antibodies have an EC50 within a factor of 2, 3 5, or 6 of that of the HDLD humanized 20F3 antibody. Preferred humanized 20F3 antibodies bind to the same epitope and/or compete with murine 20F3 for binding to human NTB-A. Here as elsewhere in this application, EC50's and Kd's can be measured in accordance with the methods of the Examples.

B. Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Human acceptor sequences can be selected for a high degree of sequence identity in the variable region frameworks with donor sequences to match canonical forms between acceptor and donor CDRs among other criteria. Suitable acceptor sequence for the heavy chains of 20F3 include IGHV7-4-1-IGHJ6. Thus, a humanized antibody is an antibody having CDRs entirely or substantially from a donor antibody and variable region framework sequences and constant regions, if present, entirely or substantially from human antibody sequences. Similarly a humanized heavy chain has usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has usually all three CDRs entirely or substantially from a donor antibody light chain, and a light chain variable region framework sequence and light chain constant region, if present, substantially from human light chain variable region framework and constant region sequences. A CDR in a humanized antibody is substantially from a corresponding CDR in a non-human antibody when at least 80%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 80%, 85%, 90%, 95% or 100% of corresponding residues defined by Kabat are identical.

Although humanized antibodies often incorporate all six CDRs (preferably as defined by Kabat or IMGT®) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region);
(4) mediates interaction between the heavy and light chains,
   or
(5) is the result of somatic mutation in the mouse chain.
(6) is a site of glycosylation.

Framework residues from classes (1)-(3) are sometimes alternately referred to as canonical and vernier residues. Framework residues defining canonical class of the donor CDR loops determining the conformation of a CDR loop are sometimes referred to as canonical residues (Chothia and Lesk, J. Mol. Biol. 196, 901-917 (1987), Thornton & Martin J. Mol. Biol., 263, 800-815, 1996). A layer of framework residues that support antigen-binding loop conformations play a role in fine-tuning the fit of an antibody to antigen are sometimes referred to as vernier residues (Foote & Winter, 1992, J Mol Bio. 224, 487-499).

The invention provides the 20F3 antibody and humanized, chimeric and veneered forms thereof. The invention provides humanized forms of the mouse 20F3 antibody including five exemplified humanized heavy chain mature variable regions (HA, HB, HC, HD and HE) (SEQ ID NOs:5-9) and four exemplified humanized light chains (LA, LB, LC and LD) (SEQ ID NOs:15-18) which can be combined in different permutations with adequate binding. Of these permutations, HDLD is preferred because it has the best combination of binding properties and an acceptable number of back mutations. HDLD also retained binding to cyno-NTB-A. HDLD also has good yield in cell culture and demonstrates little aggregation. Other combinations with EC50 within a factor of that of mouse 20F3 and fewer backmutations than HDLD include HCLB, HCLD, HDLB and HELB.

The invention provides humanized forms of the murine 20F3 antibody wherein the antibody comprises the 3 heavy chain CDRs of SEQ ID NO:3 and the 3 light chain CDRs of SEQ ID NO:13 wherein the CDRs are as defined by Kabat. The invention also provides humanized forms of the murine 20F3 antibody wherein the antibody comprises the 3 heavy chain CDRs of SEQ ID NO:3 and the 3 light chain CDRs of SEQ ID NO:13 wherein the CDRs are as defined by IMGT. The Kabat heavy chain CDRs are as set forth in SEQ ID NOs: 10-12 and the Kabat light chain CDRs are as set forth in SEQ ID NOs: 19-21. The IMGT® heavy chain CDRs are as set forth in SEQ ID NO: 22-24 and the IMGT® light chain CDRs are as set forth in SEQ ID NOs: 25-27.

The invention provides humanized forms of the murine 20F3 antibody wherein the light chain framework region is derived from human germline donor sequence vhIGKV3-11 and exon hIGKJ4 and the heavy chain is derived from human germline donor sequence hIGHV7-4-1 and exon hIGHJ6. Accordingly, humanized antibodies described herein can be humanized using the human germline donor sequence hIGKV3-11 and exon hIGKJ4 for the light chain variable region and the human germline donor sequence IGHV7-4-1 and exon hIGHJ6 for the heavy chain variable region. The CDRs can be as defined by Kabat or IMGT.

The invention provides variants of the HDLD humanized antibody in which the humanized heavy chain mature variable region shows at least 80%, 85%, 90%, 95%, 96%, 97%, 98% or 99% identity to SEQ ID NO:8 and the humanized light chain mature variable region shows at least 80%, 85%, 90%, 95%, 96%, 97%, 98% or 99% sequence identity to SEQ ID NO:18. Preferably, in such antibodies some or all of the backmutations in HDLD are retained. In some antibodies, at least 1, 2, 3, 4, 5, 6, 7, 8, 9, 10, 11 or all 12 of the following variable region frameworks positions are occupied as specified: H2 occupied by I, H44 occupied by D, H46 occupied by K, H73 occupied by K, H76 occupied by N, L1 occupied by Q, L5 occupied by S, L21 occupied by M, L46 occupied by P, L47 occupied by W, L58 occupied by V, L71 occupied by Y; numbering is via the Kabat numbering system. The CDR regions of such humanized antibodies are preferably substantially identical to the CDR regions of HDLD as defined by Kabat, which are the same as those of the mouse donor antibody. In one embodiment, the humanized antibody comprises a heavy chain comprising the 3 CDRs of SEQ ID NO:8 and variable region frameworks with at least 95% identity to the variable region frameworks of SEQ ID NO:8. In another embodiment, the humanized antibody comprises a light chain comprising the 3 CDRs of SEQ ID NO:18 and variable region frameworks with at least 95% identity to the variable region frameworks of SEQ ID NO:18.

The invention provides variants of the HDLD humanized antibody in which the humanized heavy chain mature variable region shows at least 80%, 85%, 90%, 95%, 96%, 97%, 98% or 99% identity to SEQ ID NO:8 and the humanized light chain mature variable region shows at least 80%, 85%, 90%, 95%, 96%, 97%, 98% or 99% sequence identity to SEQ ID NO:18. In some antibodies, the following variable region frameworks positions are occupied as specified: H2 occupied by I, H38 is occupied by R or K, H44 is occupied by D or G, H46 is occupied by K or E, H68 is occupied by V or A, H73 is occupied by K, H76 is occupied by N or S, H91 is occupied by Y or F, L1 is occupied by Q or E, L5 is occupied by S or T, L21 is occupied by M or L, L46 is occupied by P, L47 is occupied by W, L58 is occupied by V or I, and L71 is occupied by Y; numbering is via the Kabat numbering system. The CDR regions of such humanized antibodies are preferably substantially identical to the CDR regions of HDLD as defined by Kabat, which are the same as those of the mouse donor antibody. In one embodiment, the humanized antibody comprises a heavy chain comprising the 3 CDRs of SEQ ID NO:8 and variable region frameworks with at least 95% identity to the variable region frameworks of SEQ ID NO:8. In another embodiment, the humanized antibody comprises a light chain comprising the 3 CDRs of SEQ ID NO:18 and variable region frameworks with at least 95% identity to the variable region frameworks of SEQ ID NO:18.

Insofar as humanized 20F3 antibodies show any variation from the exemplified HDLD humanized antibody, one possibility for such additional variation is additional backmutations in the variable region frameworks. Any or all of the positions backmutated in other exemplified humanized heavy or light chain mature variable regions can be made (i.e., 1, 2, or all 3 of H38 occupied by K, H68 occupied by A, H91 occupied by F) However, such additional backmutations are not preferred because they in general do not improve affinity and introducing more mouse residues may give increased risk of immunogenicity. Variants include HALA, HALB, HALC, HALD, HBLA, HBLB, HBLC, HBLD, HCLA, HCLB, HCLC, HCLD, HDLA, HDLB, HDLC, HELA, HELB, HELC, and HELD.

Another possible variation is to substitute certain residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies, by molecular modeling and/or empirically. In such humanized antibodies at positions in which one or more donor CDR residues is absent, the amino acid occupying the position can be an amino acid occupying the corresponding position in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced HDLD amino acids. Preferably, replacements relative to HDLD (whether or not conservative) have no substantial effect on the binding affinity or potency of the humanized mAb, that is, its ability to bind human NTB-A and inhibit growth of cancer cells.

Variants typically differ from the heavy and light chain mature variable region sequences of HLD by a small number (e.g., typically no more than 1, 2, 3, 5 or 10 in either the light chain or heavy chain mature variable region, or both) of replacements, deletions or insertions.

Antibodies can be assayed for specific binding by conventional methods, including immunoassays, which include assay systems using techniques such as western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well-known in the art (see, e.g., Ausubel et al., eds, 1994, *Current Protocols in Molecular Biology*, Vol. 1, John Wiley & sons, Inc., New York). The saturation binding protocol in the examples can be used to determine specific binding.

Any of the antibodies can be selected to have the same or overlapping epitope specificity as an exemplar antibody, such as the mouse 20F3 antibody, by a competitive binding assay or otherwise. Competition between antibodies is evaluated from the ability of a test antibody to compete with a reference antibody, here mouse 20F3, for specific binding to human NTB-A. A mouse 20F3 reference antibody has heavy and light chain mature variable regions of SEQ ID NOS. 3 and 13 and is of IgG1 kappa isotype. Preferred antibodies have the same epitope specificity as the 20F3 antibody. Those of skill are able to identify an epitope bound by an antibody using a variety of methods. For example, array-based oligopeptide scanning or pepscan analysis uses a library of oligo-peptide sequences from overlapping and non-overlapping segments of a target antigen and tests for their ability to bind the antibody of interest. See, e.g., Geysen et al., PNAS 81:3998-4002 (1984). Non-linear epitopes can be identified using, e.g., CLIPS™ technology, a variation of array-based oligopeptide scanning See, e.g., Timmerman et al., Open Vaccine J. 2:56-67 (2009). The antigen protein can also be mutagenized and then use to assess binding by the antibody of interest. The protein systematic site-directed mutagenesis can be used or a library of mutations can be made and used to screen for antibody binding. Mutation libraries can be purchased from, e.g., Integral Molecular. Amide hydrogen/deuterium exchange MS can be used to identify epitopes. Antigens of interest are placed in deuterated water and labeled with deuterons. The protein is then digested with a protease and the resulting peptide fragments are subjected to mass spec analysis. The antigen is also assessed in the presence of an antibody and differences in labeling of peptide fragments indicate areas of antibody binding.

IV. Selection of Constant Region

Anti-NTBA antibodies comprising a VH and/or VL domain can be linked to at least a portion of an immunoglobulin constant region (e.g., a human immunoglobulin constant region). For example, some anti-NTB-A antibodies comprises first and second polypeptide chains, where the first polypeptide chain comprises a VH domain as described herein linked to at least a portion of an immunoglobulin heavy chain constant region and the second polypeptide chain comprises a VL domain as described herein linked to at least a portion of an immunoglobulin light chain constant region. Typically, the VH or VL domain is linked amino-terminal to an immunoglobulin constant region or portion thereof. In particular variations of an antibody comprising first and second polypeptide chains, the first and second polypeptide chains have a domain structure corresponding to the heavy and light chains of an intact native antibody, e.g., a first polypeptide (heavy) chain having the amino-terminal to carboxyl-terminal domain structure of VH-CH1-hinge-CH2-CH3 and a second polypeptide (light) chain having the amino-terminal to carboxyl-terminal domain structure of VL-CL.

Some anti-NTB-A antibody are single-chain antibodies comprising a VH domain, a VL domain, and at least a portion of an immunoglobulin constant region (e.g., a heavy chain constant region lacking a CH1 domain) linked within a single polypeptide chain. For example, the VH and VL domains may be constructed as a single-chain Fv (scFv) in either a VH/VL or VL/VH (amino-terminal/carboxyl-terminal) orientation, with the scFv linked (typically amino-terminal) to a heavy chain constant region, such as, e.g., a constant region comprising the CH2 and CH3 domains but lacking the CH1 domain. The scFv is typically linked to the constant region via a linker such as, for example, a linker derived from an immunoglobulin hinge region.

The choice of constant region can depend, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Exemplary heavy and light chain constant regions are provided by SEQ ID NOS. 27, 28 and 29. Antibodies can be expressed, e.g., as tetramers containing two light and two heavy chains, as separate heavy chains, light chains, as Fab, Fab', F(ab')2, and Fv, or as single chain antibodies in which heavy and light chain variable domains are linked through a spacer. Additionally, the constant regions can be mutated, if desired. In some aspects, a mutant form of a natural human constant region will have reduced binding to an Fcγ receptor relative to the natural human constant region.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA* 103:4005, 2006), or to prolong half-life in humans (see, e.g., Hinton et al., *J. Biol. Chem.* 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (US 20100158909; numbering of the Fc region is according to the EU index). In some aspects, the presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624,821.)

The in vivo half-life of an antibody can also impact on its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, Annu. Rev. Immunol. 18:739-766, 2000; Ghetie and Ward, Immunol. Res. 25:97-113, 2002). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, supra; Ghetie and Ward, 2002, supra). The region on human IgG1 involved in FcRn binding has been mapped (Shields et al., J. Biol. Chem. 276:6591-604, 2001). Alanine substitutions at positions Pro238, Thr256, Thr307, Gln311, Asp312, Glu380, Glu382, or Asn434 of human IgG1 enhance FcRn binding (Shields et al., supra). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Leu at position 428. EU numbering is used for all position in the constant region.

Oligosaccharides covalently attached to the conserved Asn297 are involved in the ability of the Fc region of an IgG to bind FcγR (Lund et al., J. Immunol. 157:4963-69, 1996; Wright and Morrison, Trends Biotechnol. 15:26-31, 1997). Engineering of this glycoform on IgG can significantly improve IgG-mediated ADCC. Addition of bisecting N-acetylglucosamine modifications (Umana et al., Nat. Biotechnol. 17:176-180, 1999; Davies et al., Biotech. Bioeng. 74:288-94, 2001) to this glycoform or removal of fucose (Shields et al., J. Biol. Chem. 277:26733-40, 2002; Shinkawa et al., J. Biol. Chem. 278:6591-604, 2003; Niwa et al., Cancer Res. 64:2127-33, 2004) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., J. Biol. Chem. 276:6591-604, 2001). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, supra; Okazaki et al., J. Mol. Biol. 336:1239-49, 2004).

Complement fixation activity of antibodies (both C1q binding and CDC activity) can be improved by substitutions at Lys326 and Glu333 (Idusogie et al., J. Immunol. 166:2571-2575, 2001). The same substitutions on a human IgG2 backbone can convert an antibody isotype that binds poorly to C1q and is severely deficient in complement activation activity to one that can both bind C1q and mediate CDC (Idusogie et al., supra). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., J. Immunol. 154:2226-36, 1995). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., J. Immunol. 148:2918-22, 1992). In addition, a bispecific diabody construct with specificity for C1q also confers CDC activity (Kontermann et al., Nat. Biotech. 15:629-31, 1997).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity. Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P311S (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRn.

V. Nucleic Acids and Methods of Production

The invention further provides nucleic acids encoding any of the VH and/or VL domains described above, including polypeptides comprising the VH and/or VL domains linked to additional polypeptide segments such, for example, polypeptide segments corresponding to an immunoglobulin constant region. Typically, the nucleic acids also encode a signal peptide fused amino-terminal to the mature polypeptide comprising the VH and/or VL domains. Coding sequences on nucleic acids can be in operable linkage with regulatory sequences to ensure expression of the coding sequences, such as a promoter, enhancer, ribosome binding site, transcription termination signal and the like. The nucleic acids can occur in isolated form or can be cloned into one or more vectors. The nucleic acids can be synthesized by for example, solid state synthesis or PCR of overlapping oligonucleotides. Nucleic acids encoding both a VH domain and a VL domain (e.g., in the context of antibodies comprising separate heavy and light chains) can be joined as one contiguous nucleic acid, e.g., within an expression vector, or can be separate, e.g., each cloned into its own expression vector.

Anti-NTB-A antibodies are typically produced by recombinant expression of one or more nucleic acids encoding one or more antibody chains. Recombinant polynucleotide constructs typically include an expression control sequence operably linked to the coding sequences of one or more polypeptide chains comprising VH and/or VL domains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies.

For the expression of antibodies comprising first and second polypeptide chains (e.g., heavy and light chains), the two polypeptide chains can be co-expressed from separate vectors in the host cell for expression of the entire antibody molecule. Alternatively, two polypeptide chains can be co-expressed from separate expression units in the same vector in the host cell for expression of the entire antibody molecule.

Mammalian cells are a preferred host for expressing nucleotide segments encoding immunoglobulins or fragments thereof. See Winnacker, *From Genes to Clones*, (VCH Publishers, NY, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are non-human. Expression vectors for these cells can include expression control sequences, such as an origin of replication, a promoter, an enhancer (Queen et al., *Immunol. Rev.* 89:49, 1986), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149, 1992.

Once expressed, antibodies can be purified according to standard procedures of the art, including HPLC purification, column chromatography, gel electrophoresis and the like (see generally Scopes, *Protein Purification* (Springer-Verlag, NY, 1982)).

VI. Antibody Drug Conjugates

Anti-NTB-A antibodies can be conjugated to cytotoxic or cytostatic moieties to form antibody drug conjugates (ADCs). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-NTB-A antibody can be conjugated to a cytotoxic agent such as a chemotherapeutic agent, or a toxin (e.g., a cytostatic or cytocidal agent such as, for example, abrin, ricin A, pseudomonas exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[1,4] benzodiazepines, indolinobenzodiazepines, and oxazolidinobenzodiazepines including pyrrolo[1,4]benzodiazepine dimers, indolinobenzodiazepine dimers, and oxazolidinobenzodiazepine dimers) and vinca alkaloids.

An anti-NTB-A antibody can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, (β-lactamase, β-glucosidase, nitroreductase and carboxypeptidase A.

Techniques for conjugating therapeutic agents to proteins, and in particular to antibodies, are well-known. (See, e.g., Alley et al., *Current Opinion in Chemical Biology* 2010 14:1-9; Senter, *Cancer J.*, 2008, 14(3):154-169.) The therapeutic agent can be conjugated in a manner that reduces its activity unless it is cleaved off the antibody (e.g., by hydrolysis, by proteolytic degradation, or by a cleaving agent). In some aspects, the therapeutic agent is attached to the antibody with a cleavable linker that is sensitive to cleavage in the intracellular environment of the NTB-A-expressing cancer cell but is not substantially sensitive to the extracellular environment, such that the conjugate is cleaved from the antibody when it is internalized by the NTB-A-expressing cancer cell (e.g., in the endosomal or, for example by virtue of pH sensitivity or protease sensitivity, in the lysosomal environment or in the caveolear environment). In some aspects, the therapeutic agent can also be attached to the antibody with a non-cleavable linker.

Typically the ADC comprises a linker region between the cytotoxic or cytostatic agent and the anti-NTB-A antibody. As noted supra, typically, the linker can be cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, *Pharm. Therapeutics* 83:67-123, 1999). Most typical are peptidyl linkers that are cleavable by enzymes that are present in NTB-A-expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide).

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, *Pharm. Therapeutics* 83:67-123, 1999; Neville et al., *Biol. Chem.* 264:14653-14661, 1989.) Such linkers are relatively stable under neutral pH conditions, such as those in the blood, but are unstable at below pH 5.5 or 5.0, the approximate pH of the lysosome.

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., *Cancer Res.* 47:5924-5931, 1987; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

The linker can also be a malonate linker (Johnson et al., *Anticancer Res.* 15:1387-93, 1995), a maleimidobenzoyl linker (Lau et al., *Bioorg-Med-Chem.* 3:1299-1304, 1995), or a 3'-N-amide analog (Lau et al., *Bioorg-Med-Chem.* 3:1305-12, 1995).

The linker also can be a non-cleavable linker, such as an maleimido-alkylene- or maleimide-aryl linker that is directly attached to the therapeutic agent and released by proteolytic degradation of the antibody.

Typically, the linker is not substantially sensitive to the extracellular environment, meaning that no more than about 20%, typically no more than about 15%, more typically no more than about 10%, and even more typically no more than about 5%, no more than about 3%, or no more than about 1% of the linkers in a sample of the ADC is cleaved when the ADC is present in an extracellular environment (e.g., in plasma). Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

will be conjugated to the linker via a sulfur atom of a cysteine residue. Methods of conjugating linker and drug-linkers to antibodies are known in the art.

Exemplary antibody-drug conjugates include auristatin based antibody-drug conjugates meaning that the drug component is an auristatin drug. Auristatins bind tubulin, have been shown to interfere with microtubule dynamics and nuclear and cellular division, and have anticancer activity. Typically the auristatin based antibody-drug conjugate comprises a linker between the auristatin drug and the anti-NTB-A antibody. The linker can be, for example, a cleavable linker (e.g., a peptidyl linker) or a non-cleavable linker (e.g., linker released by degradation of the antibody). Auristatins include MMAF, and MMAE. The synthesis and structure of exemplary auristatins are described in U.S. Publication Nos. 2009-0111756, 2009-0018086, and U.S. Pat. Nos. 7,659,241, 7,498,298, 7,968,687 each of which is incorporated herein by reference in its entirety and for all purposes.

Other exemplary antibody-drug conjugates include maytansinoid antibody-drug conjugates meaning that the drug component is a maytansinoid drug, and benzodiazepine antibody drug conjugates meaning that the drug component is a benzodiazepine (e.g., pyrrolo[1,4]benzodiazepine dimers, indolinobenzodiazepine dimers, and oxazolidino-benzodiazepine dimers).

The present inventors have found a humanized NTB-A targeted ADC comprising a PBD drug-linker is particularly effective.

A preferred PBD for use in the present invention is represented by formula I. The preferred stereochemistry of the PBD drug component is as shown in formula Ia:

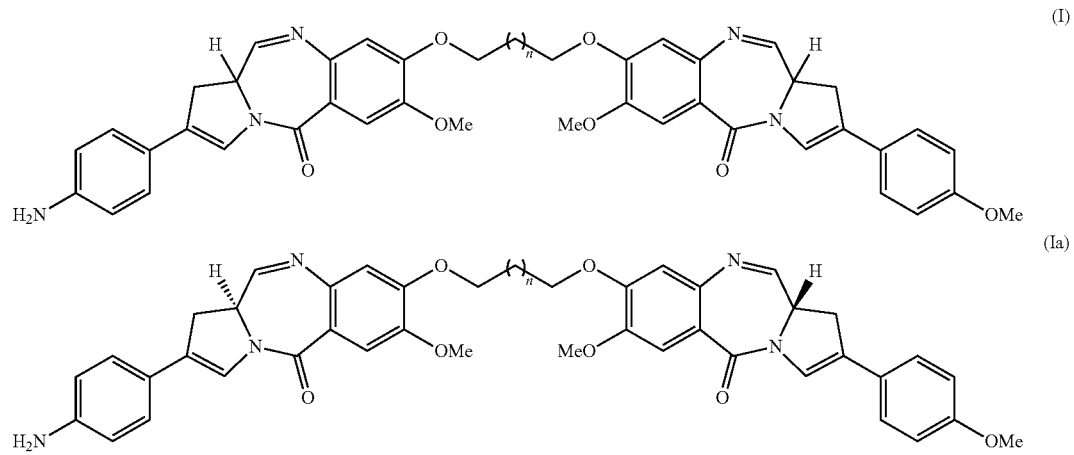

The linker can also promote cellular internalization. The linker can promote cellular internalization when conjugated to the therapeutic agent (i.e., in the milieu of the linker-therapeutic agent moiety of the ADC or ADC derivate as described herein). Alternatively, the linker can promote cellular internalization when conjugated to both the therapeutic agent and the anti-NTB-A antibody (i.e., in the milieu of the ADC as described herein).

The anti-NTB-A antibody can be conjugated to the linker via a heteroatom of the antibody. These heteroatoms can be present on the antibody in its natural state or can be introduced into the antibody. In some aspects, the NTB-A antibody will be conjugated to the linker via a nitrogen atom of a lysine residue. In other aspects, the NTB-A antibody or a pharmaceutically salt, solvate, or solvate of the salt; wherein the subscript n is 1 or 3.

The PBD dimer of formula I (or a pharmaceutically salt, solvate, or solvate of the salt thereof) is typically linked to the antibody via a Linker Unit, LU. The Linker Unit acts to release the PBD dimer of formula I (or a pharmaceutically salt, solvate, or solvate of the salt thereof) at the target site (e.g., inside the cancer cell). A PBD drug-linker compound for use in the present invention is represented below by formula II (preferred stereochemistry as shown in IIa) wherein LU is a Linker Unit. The Linker Unit can be, for example, a cleavable peptide Linker Unit (e.g., a linker comprising the valine-alanine peptide) or a cleavable disulfide Linker Unit:

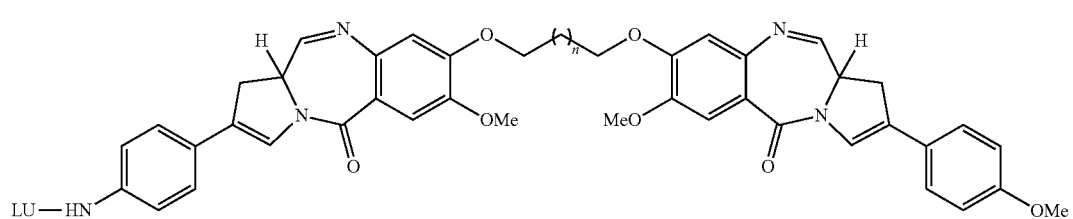

(II)

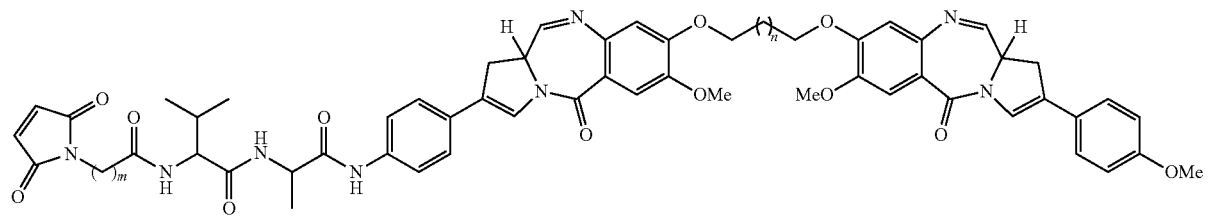

(IIa)

or a pharmaceutically salt, solvate, or solvate of the salt; wherein the subscript n is 1 or 3.

A preferred PBD drug-linker compound for use in the present invention is represented by Formula III below:

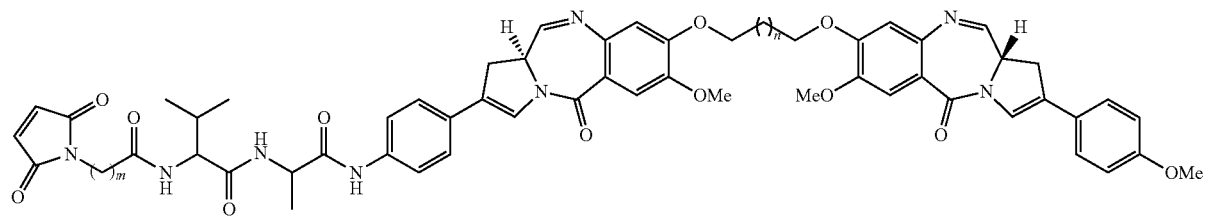

(III)

or a pharmaceutically salt, solvate, or solvate of the salt; wherein the subscript n is 1 or 3 and the subscript m is an integer from 2 to 5.

The preferred stereochemistry of the PBD drug component of the drug-linker is as shown in Formula IIIa below:

(IIIa)

The preferred stereochemistry of the PBD drug and linker components of the SGD-1910 PBD drug-linker is as shown in Formula IIIb below:

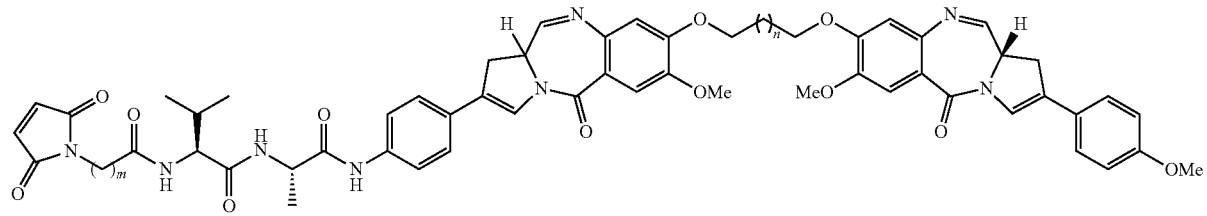

(IIIb)

The PBD drug-linker is conjugated to a 20F3 antibody, including veneered, chimeric and humanized forms thereof to produce a NTB-A targeted antibody-drug conjugate. For example, the antibody can be conjugated to a drug-linker of formula II or formula III. An exemplary NTB-A targeted antibody-drug conjugate is shown below in formulas IV, IVa, and IVb:

antibody in the population) is an important quality attribute as it determines the amount of drug that can be delivered to a target cell. The average drug load can be an integer or non-integer value but is typically a non-integer value.

The heterogeneity of an antibody-drug conjugate composition will, in some aspects, be dependent on the conjugation technology used to conjugate drug-linker molecules to anti-

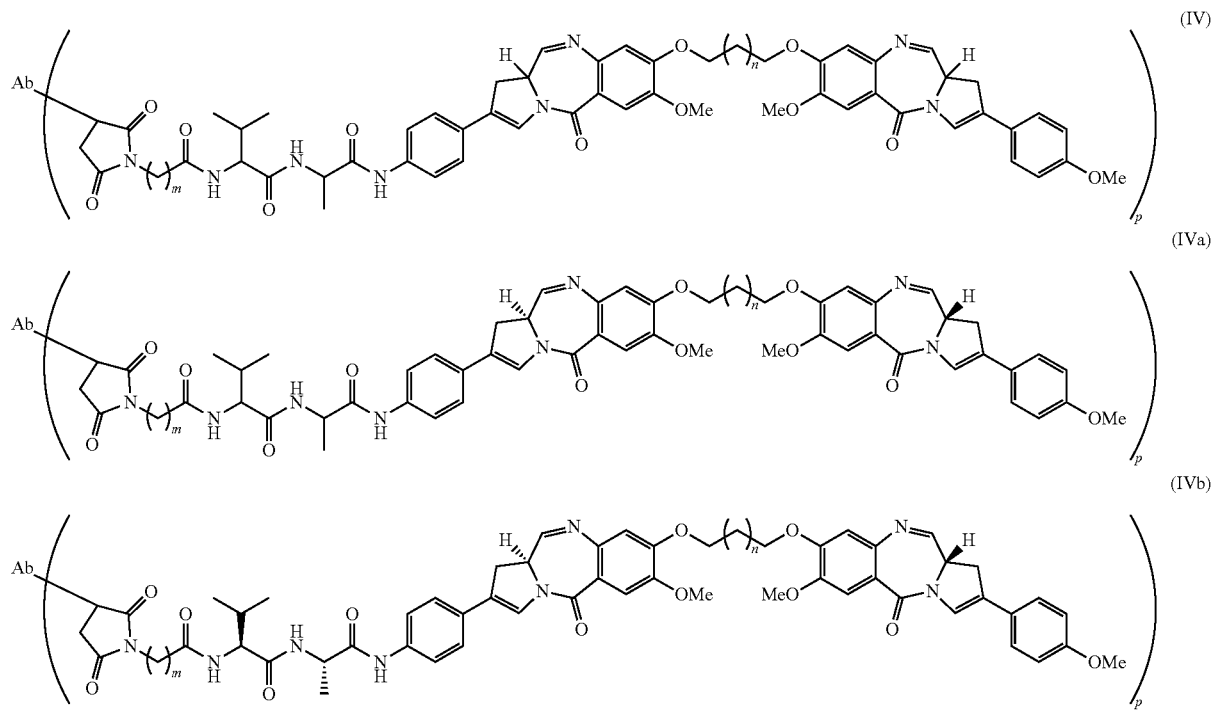

or a pharmaceutically salt, solvate, or solvate of the salt; wherein the subscript n is 1 or 3; the subscript m is an integer from 2 to 5; and the subscript p is an integer from 1 to 4.

The present invention provides compositions, including pharmaceutical compositions comprising anti-NTBA antibody drug conjugates, including those particularly exemplified herein. The compositions typically include a population of antibody drug conjugate molecules.

Drug Loading—"p"

Referring to the NTB-A targeted antibody-drug conjugates of formulas IV, IVa, and IVb, the subscript p represents the drug load for an antibody molecule (number of molecules of drug attached to an antibody molecule) and is an integer value. In a composition comprising a population of antibody-drug conjugate molecules, the average drug load (e.g., the average number of drug-linker molecules per body molecules. For example, in some aspects, the conjugation technology used to conjugate the drug-linker molecules to the antibody molecules will result in an antibody-drug conjugate composition that is heterogenous with respect to the distribution of drug-linker molecules on the antibody and/or with respect to number of drug-linkers on the antibody molecules (e.g., when conjugating via interchain disulfides using non-site specific technology). In other aspects, the conjugation technology used to conjugate the drug-linker molecules will result in an antibody-drug conjugate composition that is substantially homogenous with respect to the distribution of drug-linker molecules on the ligand molecules and/or with respect to number of drug-linkers molecules on the antibody molecules (e.g., when using site specific conjugation technology). With both site specific and non-site specific methods, there may also be a small percentage of unconjugated antibody molecules. The percentage of unconjugated antibody molecules is included in the average drug load value.

In preferred aspects of the present invention, the average drug load when referring to a composition comprising a population of antibody-drug conjugate compounds is from about 2 to about 14, preferably about 2 to about 10. For PBD antibody drug conjugates, such as those exemplified herein, a particularly preferred average drug load is about 2. In some aspects, the actual drug load for individual antibody molecules in the population of antibody-drug conjugate compounds is from 1 to 4, 1 to 3 or 1 to 2 with a predominant drug loading of 2. In preferred aspects, the average drug load of 2 is achieved via site specific conjugation techniques (e.g., engineered cysteines introduced to the antibody including at position 239, according to the EU Index numbering system).

In other aspects of the present invention, the average drug load when referring to a composition comprising a population of PBD antibody-drug conjugate compounds is about 3 or about 4 and the actual drug load for individual antibody molecules in the population of antibody-drug conjugate compounds is from 1 to 6, 1 to 5 1 to 4 or 1 to 3.

The average number of Drug-Linker units per Ligand unit in a preparation from a conjugation reaction may be characterized by conventional means such as mass spectroscopy, ELISA assay, HIC and HPLC. The quantitative distribution of Ligand-Linker-Drug conjugates in terms of p may also be determined. In some instances, separation, purification, and characterization of homogeneous Ligand-Drug Conjugates, where p is a certain value from Ligand-Drug Conjugate with other drug loadings may be achieved by means such as reverse phase HPLC or electrophoresis.

VII. Applications

The anti-NTBA-antibodies described herein, as naked antibodies, or as antibody drug conjugates, can be used in methods for the treatment of a disease or disorder associated with an NTB-A-expressing cell.

For example, the anti-NTBA antibodies described herein, as naked antibodies, or as antibody drug conjugates, can be used to treat an NTB-A-expressing cancer. Some such cancers show detectable levels of NTB-A measured at either the protein (e.g., by immunoassay using one of the exemplified antibodies) or mRNA level. Some such cancers show elevated levels of NTB-A relative to noncancerous tissue of the same type, preferably from the same patient. An exemplary level of NTB-A on cancer cells amenable to treatment is 5000-150000 NTB-A molecules per cell, although higher or lower levels can be treated. Optionally, a level of NTB-A in a cancer is measured before performing treatment.

Examples of cancers associated with NTB-A expression and amenable to treatment with the naked antibodies or antibody drug conjugates disclosed herein include hematological malignancies, including B-cell, T-cell, and NK-cell malignancies. In an embodiment, the naked antibodies or antibody drug conjugates disclosed herein bind receptors on NK cells, triggering cytolytic activity and proliferation, which stimulates anti-tumor activity of the patient's immune system. In some methods of treatment, the patient has a cancer, which is a multiple myeloma, an acute myeloid leukemia (AML), a chronic lymphocytic leukemia (CLL), a T-Cell leukemia, a T-Cell or B-cell lymphoma such as, e.g., a non-Hodgkin's lymphoma (NHL), or myeloma related malignacies such as primary amyloidosis, Waldenström's macroglobulinemia, or high risk MGUS (monoclonal gammopathy of undetermined significance). The treatment can be applied to patients having primary or metastatic tumors of these kinds. The treatment can also be applied to patients who are refractory to conventional treatments, or who have relapsed following a response to such treatments.

The anti-NTBA antibodies disclosed herein, as naked antibodies, or as antibody drug conjugates, can be used to treat autoimmune diseases and inflammatory disease. Diseases and disorders treatable by the present methods include those associated with B cells, e.g., those diseases characterized by excessive numbers of B cells, overactive B cells, or dysfunctional B cells. These diseases include inflammatory diseases and autoimmune disease. Exemplary diseases treatable by the present methods include rheumatoid arthritis, systemic lupus erythematosus, multiple sclerosis, inflammatory bowel disease, asthma, allergy, celiac disease, graft-versus-host disease, and transplant rejection.

The present antibodies against NTB-A, as naked antibodies or as antibody drug conjugates, can be used as a monotherapy or in combination therapy with, for example, standard of care for treatment of such diseases and/or disorders. Accordingly, methods for the treatment of cancer include administering to a patient in need thereof an effective amount of a naked antibody or antibody drug conjugate as described herein as a monotherapy or in combination with an additional anti-cancer agent or other agent to alleviate symptoms of the cancer. Methods for the treatment of autoimmune disease include administering to a patient in need thereof an effective amount of a naked antibody or antibody drug conjugate as described herein as a monotherapy or in combination with an additional therapeutic agent for the treatment of autoimmune disease. Methods for the treatment of inflammatory disease include administering to a patient in need thereof an effective amount of a naked antibody or antibody drug conjugate as described herein as a monotherapy or in combination with an additional therapeutic agent for the treatment of inflammatory disease.

An exemplary agent for combination therapy is carfilzomib (e.g. KYPROLIS®), a proteasome inhibitor used to treat multiple myeloma (see Siegel D S et al. A phase 2 study of single-agent carfilzomib (PX-171-003-A1) in patients with relapsed and refractory multiple myeloma. *Blood* 2012; 120:2817-2825). Carfilzomib can be administered as an intravenous/IV infusion. In an embodiment, carfilzomib is administered in a combination therapy with an NTB-A directed antibody-drug conjugate of the present invention. In a further embodiment, carfilzomib is administered in a combination therapy with humanized 20F3 antibody-drug conjugate of the present invention. In a further embodiment, carfilzomib is administered in a combination therapy with a h20F3ec-1910(2) of the present invention.

Carfilzomib can also be administered in a combination therapy with an NTB-A directed antibody-drug conjugate of the present invention and an additional agent. Carfilzomib has been combined with various additional agents to treat multiple myeloma. For example, carfilzomib has been combined with lenalidomide and dexamethasone (see Stewart K A et al. Carfilzomib, lenalidomide, and dexamethasone for relapsed multiple myeloma. *N Engl J Med.* 2015; 372:142-152). In an embodiment, carfilzomib is administered in a combination therapy with lenalidomide, dexamethasone, and an NTB-A directed antibody-drug conjugate of the present invention. In a further embodiment, carfilzomib is administered in a combination therapy with lenalidomide, dexamethasone, and a humanized 20F3 antibody-drug conjugate of the present invention. In a further embodiment, carfilzomib is administered in a combination therapy with lenalidomide, dexamethasone, and a h20F3ec-1910(2) of the present invention.

Carfilzomib has also been combined with dexamethasone (see Dimopoulos MD et al. Carfilzomib and dexamethasone versus bortezomib and dexamethasone for patients with relapsed or refractory multiple myeloma (ENDEAVOR): a randomised, phase 3, open-label, multicentre study. *Lancet Oncology* 2016; 17:27-38). In an embodiment, carfilzomib is administered in a combination therapy with dexamethasone and an NTB-A directed antibody-drug conjugate of the present invention. In a further embodiment, carfilzomib is administered in a combination therapy with dexamethasone and a humanized 20F3 antibody-drug conjugate of the present invention. In a further embodiment, carfilzomib is administered in a combination therapy with dexamethasone and a h20F3ec-1910(2) of the present invention.

Carfilzomib has also been combined with panobinostat (see Berdeja J G et al. Phase I/II study of the combination of panobinostat and carfilzomib in patients with relapsed/refractory multiple myeloma. *Haematologica* 2015; 100: 670-676). In an embodiment, carfilzomib is administered in a combination therapy with panobinostat and an NTB-A directed antibody-drug conjugate of the present invention. In a further embodiment, carfilzomib is administered in a combination therapy with panobinostat and a humanized 20F3 antibody-drug conjugate of the present invention. In a further embodiment, carfilzomib is administered in a combination therapy with panobinostat and a h20F3ec-1910(2) of the present invention.

Carfilzomib has also been combined with pomalidomide and dexamethasone (see Shah J et al. Carfilzomib, pomalidomide, and dexamethasone (CPD) in patients with relapsed and/or refractory multiple myeloma. Blood 2015; 126: 2284-2290). In an embodiment, carfilzomib is administered in a combination therapy with pomalidomide, dexamethasone, and an NTB-A directed antibody-drug conjugate of the present invention. In a further embodiment, carfilzomib is administered in a combination therapy with pomalidomide, dexamethasone, and a humanized 20F3 antibody-drug conjugate of the present invention. In a further embodiment, carfilzomib is administered in a combination therapy with pomalidomide, dexamethasone, and a h20F3ec-1910(2) of the present invention.

Another exemplary agent for combination therapy is daratumumab (e.g. DARZALEX™), a human monoclonal antibody that binds CD38 (a glycoprotein highly expressed on multiple myeloma cells). Daratumumab can be administered to patients by intravenous infusion to treat multiple myeloma (see Lokhorst H M et al. Targeting CD38 with daratumumab monotherapy in multiple myeloma. *N Engl J Med* 2015; 373:1207-1219). In an embodiment, daratumumab is administered in a combination therapy with an NTB-A directed antibody-drug conjugate of the present invention. In a further embodiment, daratumumab is administered in a combination therapy with a humanized 20F3 antibody-drug conjugate of the present invention. In a further embodiment, daratumumab is administered in a combination therapy with a h20F3ec-1910(2) of the present invention.

Daratumumab can also be administered in a combination therapy with an NTB-A directed antibody-drug conjugate of the present invention and an additional agent. Daratumumab has been combined with various additional agents to treat multiple myeloma. For example, daratumumab has been combined with bortezomib and lenalidomide (see Phipps C et al. Daratumumab and its potential in the treatment of multiple myeloma: overview of the preclinical and clinical development. *Ther Adv Hematol* 2015; 6:120-127). In an embodiment, daratumumab is administered in a combination therapy with bortezomib, lenalidomide, and an NTB-A directed antibody-drug conjugate of the present invention. In a further embodiment, daratumumab is administered in a combination therapy with bortezomib, lenalidomide, and a humanized 20F3 antibody-drug conjugate of the present invention. In a further embodiment, daratumumab is administered in a combination therapy with bortezomib, lenalidomide, and a h20F3ec-1910(2) of the present invention.

Daratumumab has also been combined with bortezomib and dexamethasone (see Phipps C et al.). In an embodiment, daratumumab is administered in a combination therapy with bortezomib, dexamethasone, and an NTB-A directed antibody-drug conjugate of the present invention. In a further embodiment, daratumumab is administered in a combination therapy with bortezomib, dexamethasone, and a humanized 20F3 antibody-drug conjugate of the present invention. In a further embodiment, daratumumab is administered in a combination therapy with bortezomib, dexamethasone, and a h20F3ec-1910(2) of the present invention.

Another exemplary agent for combination therapy is elotuzumab (e.g. EMPLICITI™), a monoclonal antibody that binds CD319, or signaling lymphocytic activation molecule F7 (SLAMF7), a marker for malignant multiple myeloma cells. Elotuzumab can be administered to patients by intravenous infusion to treat multiple myeloma (see Zonder J A et al. A phase 1, multicenter, open-label, dose escalation study of elotuzumab in patients with advanced multiple myeloma. *Blood* 2012; 120: 552-559). In an embodiment, elotuzumab is administered in a combination therapy with an NTB-A directed antibody-drug conjugate of the present invention. In a further embodiment, elotuzumab is administered in a combination therapy with a humanized 20F3 antibody-drug conjugate of the present invention. In a further embodiment, elotuzumab is administered in a combination therapy with a h20F3ec-1910(2) of the present invention.

Elotuzumab can also be administered in a combination therapy with an NTB-A directed antibody-drug conjugate of the present invention and an additional agent. Elotuzumab has been combined with various additional agents to treat multiple myeloma. For example, elotuzumab has been combined with lenalidomide and dexamethasone (see Lonial S et al. Elotuzumab therapy for relapsed or refractory multiple myeloma. *N Engl J Med* 2015; 373:621-631). In an embodiment, elotuzumab is administered in a combination therapy with lenalidomide, dexamethasone, and an NTB-A directed antibody-drug conjugate of the present invention. In a further embodiment, elotuzumab is administered in a combination therapy with lenalidomide, dexamethasone, and a humanized 20F3 antibody-drug conjugate of the present invention. In a further embodiment, elotuzumab is administered in a combination therapy with lenalidomide, dexamethasone, and a h20F3ec-1910(2) of the present invention.

Another exemplary agent for combination therapy is lenalidomide (e.g. REVLIMID®), an immunomodulatory agent given to patients to treat multiple myeloma (see Richardson P G, A randomized phase 2 study of lenalidomide therapy for patients with relapsed or relapsed and refractory multiple myeloma. *Blood* 2006, 108: 3458-3464). Lenalidomide can be packaged as a capsule, pill, or tablet for oral administration. In an embodiment, lenalidomide is administered in a combination therapy with an NTB-A directed antibody-drug conjugate of the present invention. In a further embodiment, lenalidomide is administered in a combination therapy with a humanized 20F3 antibody-drug conjugate of the present invention. In a further embodiment, lenalidomide is administered in a combination therapy with a h20F3ec-1910(2) of the present invention.

Lenalidomide can also be administered in a combination therapy with an NTB-A directed antibody-drug conjugate of the present invention and an additional agent. Lenalidomide has been combined with various additional agents that treat multiple myeloma. For example, lenalidomide has been combined with bortezomib and dexamethasone (see Richardson P G et al. Lenalidomide, bortezomib, and dexamethasone combination therapy in patients with newly diagnosed multiple myeloma. *Blood* 2010; 116:679-686). In an embodiment, lenalidomide is administered in a combination therapy with bortezomib, dexamethasone, and an NTB-A directed antibody-drug conjugate of the present invention. In a further embodiment, lenalidomide is administered in a combination therapy with bortezomib, dexamethasone, and a humanized 20F3 antibody-drug conjugate of the present invention. In a further embodiment, lenalidomide is administered in a combination therapy with bortezomib, dexamethasone, and a h20F3ec-1910(2) of the present invention.

Lenalidomide has also been combined with carfilzomib and dexamethasone (see Stewart K A et al.). In an embodiment, lenalidomide is administered in a combination therapy with carfilzomib, dexamethasone, and an NTB-A directed antibody-drug conjugate of the present invention. In a further embodiment, lenalidomide is administered in a combination therapy with carfilzomib, dexamethasone, and a humanized 20F3 antibody-drug conjugate of the present invention. In a further embodiment, lenalidomide is administered in a combination therapy with carfilzomib, dexamethasone, and a h20F3ec-1910(2) of the present invention.

Lenalidomide has also been combined with daratumumab and bortezomib (see Phipps C et al.). In an embodiment, lenalidomide is administered in a combination therapy with daratumumab, bortezomib, and an NTB-A directed antibody-drug conjugate of the present invention. In a further embodiment, lenalidomide is administered in a combination therapy with daratumumab, bortezomib, and a humanized 20F3 antibody-drug conjugate of the present invention. In a further embodiment, lenalidomide is administered in a combination therapy with daratumumab, bortezomib, and a h20F3ec-1910(2) of the present invention.

Lenalidomide has also been combined with elotuzumab and dexamethasone (see Lonial S et al. Elotuzumab therapy for relapsed or refractory multiple myeloma. *N Engl J Med* 2015; 373:621-631). In an embodiment, lenalidomide is administered in a combination therapy with elotuzumab, dexamethasone, and an NTB-A directed antibody-drug conjugate of the present invention. In a further embodiment, lenalidomide is administered in a combination therapy with elotuzumab, dexamethasone, and a humanized 20F3 antibody-drug conjugate of the present invention. In a further embodiment, lenalidomide is administered in a combination therapy with elotuzumab, dexamethasone, and a h20F3ec-1910(2) of the present invention.

Another exemplary agent for combination therapy is bortezomib (e.g. VELCADE®), a proteasome inhibitor given to patients to treat multiple myeloma and mantle cell lymphoma (see Richardson P G et al. A phase 2 study of bortezomib in relapsed, refractory myeloma. *N Engl J Med* 2003; 348:2609-2617). Bortezomib can be administered to patients via intravenous injection. In an embodiment, bortezomib is administered in a combination therapy with an NTB-A directed antibody-drug conjugate of the present invention. In a further embodiment, bortezomib is administered in a combination therapy with a humanized 20F3 antibody-drug conjugate of the present invention. In a further embodiment, bortezomib is administered in a combination therapy with a h20F3ec-1910(2) of the present invention.

Bortezomib can also be administered in a combination therapy with an NTB-A directed antibody-drug conjugate of the present invention and an additional agent. Bortezomib has been combined with various additional agents to treat multiple myeloma. For example, bortezomib has been combined with thalidomide and dexamethasone (see Kapoor P et al. Bortezomib combination therapy in multiple myeloma. *Semin Hematol* 2012; 3:228-242). In an embodiment, bortezomib is administered in a combination therapy with thalidomide, dexamethasone, and an NTB-A directed antibody-drug conjugate of the present invention. In a further embodiment, bortezomib is administered in a combination therapy with thalidomide, dexamethasone, and a humanized 20F3 antibody-drug conjugate of the present invention. In a further embodiment, bortezomib is administered in a combination therapy with thalidomide, dexamethasone, and a h20F3ec-1910(2) of the present invention.

Bortezomib has also been combined with dexamethasone, thalidomide, cisplatin, doxorubicin, cyclophosphamide, and etoposide (see Kapoor P et al.). In an embodiment, bortezomib is administered in a combination therapy with dexamethasone, thalidomide, cisplatin, doxorubicin, cyclophosphamide, etoposide, and an NTB-A directed antibody-drug conjugate of the present invention. In a further embodiment, bortezomib is administered in a combination therapy with dexamethasone, thalidomide, cisplatin, doxorubicin, cyclophosphamide, etoposide, and a humanized 20F3 antibody-drug conjugate of the present invention. In a further embodiment, bortezomib is administered in a combination therapy with dexamethasone, thalidomide, cisplatin, doxorubicin, cyclophosphamide, etoposide, and a h20F3ec-1910(2) of the present invention.

Bortezomib has also been combined with daratumumab and lenalidomide (see Phipps C et al.). In an embodiment, bortezomib is administered in a combination therapy with daratumumab, lenalidomide, and an NTB-A directed antibody-drug conjugate of the present invention. In a further embodiment, bortezomib is administered in a combination therapy with daratumumab, lenalidomide, and a humanized 20F3 antibody-drug conjugate of the present invention. In a further embodiment, bortezomib is administered in a combination therapy with daratumumab, lenalidomide, and a h20F3ec-1910(2) of the present invention.

Bortezomib has also been combined with lenalidomide and dexamethasone (see Richardson P G et al. 2010). In an embodiment, bortezomib is administered in a combination therapy with lenalidomide, dexamethasone, and an NTB-A directed antibody-drug conjugate of the present invention. In a further embodiment, bortezomib is administered in a combination therapy with lenalidomide, dexamethasone, and a humanized 20F3 antibody-drug conjugate of the present invention. In a further embodiment, bortezomib is administered in a combination therapy with lenalidomide, dexamethasone, and a h20F3ec-1910(2) of the present invention.

Bortezomib has also been combined with panobinostat and dexamethasone (see Richardson P et al. PANORAMA 2: panobinostat in combination with bortezomib and dexamethasone in patients with relapsed and bortezomib-refractory myeloma. Blood 2013: 122:2331-2337). In an embodiment, bortezomib is administered in a combination therapy with panobinostat, dexamethasone, and an NTB-A directed antibody-drug conjugate of the present invention. In a further embodiment, bortezomib is administered in a combination therapy with panobinostat, dexamethasone, and a humanized 20F3 antibody-drug conjugate of the present invention. In a further embodiment, bortezomib is administered in a combination therapy with panobinostat, dexamethasone, and a h20F3ec-1910(2) of the present invention.

Another exemplary agent for combination therapy is dexamethasone (e.g. DECADRON®), a glucocorticosteroid used to treat cancer (including multiple myeloma, leukemia, and lymphoma), inflammation, allergies, and nausea. Dexamethasone can be administered as a tablet, pill, or capsule for oral administration, or by intravenous infusion. In an embodiment, dexamethasone is administered in a combination therapy with an NTB-A directed antibody-drug conjugate of the present invention. In a further embodiment, dexamethasone is administered in a combination therapy with a humanized 20F3 antibody-drug conjugate of the present invention. In a further embodiment, dexamethasone is administered in a combination therapy with a h20F3ec-1910(2) of the present invention. Dexamethasone can also be administered in a combination therapy with an NTB-A directed antibody-drug conjugate of the present invention and an additional agent.

Another exemplary agent for combination therapy is cyclophosphamide (e.g. CYTOXAN®), an alkylating agent used to treat cancer (including multiple myeloma, acute myelocytic leukemia, Hodgkin's and non-Hodgkin's lymphoma, breast cancer, and lung cancer, among others). Cyclophosphamide can be administered by injection, infusion, as a tablet, pill, or capsule for oral administration, or by injection into a muscle, into the abdominal lining, or into lung lining. In an embodiment, cyclophosphamide is administered in a combination therapy with an NTB-A directed antibody-drug conjugate of the present invention. In a further embodiment, cyclophosphamide is administered in a combination therapy with a humanized 20F3 antibody-drug conjugate of the present invention. In a further embodiment, cyclophosphamide is administered in a combination therapy with a h20F3ec-1910(2) of the present invention. Cyclophosphamide can also be administered in a combination therapy with an NTB-A directed antibody-drug conjugate of the present invention and an additional agent.

Another exemplary agent for combination therapy is melphalan, an alkylating agent used to treat cancer (including multiple myeloma and ovarian cancer). Melphalan can be administered orally, as an injection or infusion. In an embodiment, melphalan is administered in a combination therapy with an NTB-A directed antibody-drug conjugate of the present invention. In a further embodiment, melphalan is administered in a combination therapy with a humanized 20F3 antibody-drug conjugate of the present invention. In a further embodiment, melphalan is administered in a combination therapy with a h20F3ec-1910(2) of the present invention. Melphalan can also be administered in a combination therapy with an NTB-A directed antibody-drug conjugate of the present invention and an additional agent.

Another exemplary agent for combination therapy is pomalidomide (e.g. POMALYST®), an immunomodulatory agent used to treat multiple myeloma. Pomalidomide can be administered as a capsule, pill, or tablet for oral administration. In an embodiment, pomalidomide is administered in a combination therapy with an NTB-A directed antibody-drug conjugate of the present invention. In a further embodiment, pomalidomide is administered in a combination therapy with a humanized 20F3 antibody-drug conjugate of the present invention. In a further embodiment, pomalidomide is administered in a combination therapy with a h20F3ec-1910(2) of the present invention.

Pomalidomide can also be administered in a combination therapy with an NTB-A directed antibody-drug conjugate of the present invention and an additional agent. Pomalidomide has been combined with various additional agents to treat multiple myeloma. Pomalidomide has been combined with dexamethasone (see Richardson P et al. Pomalidomide alone or in combination with low-dose dexamethasone in relapsed and refractory multiple myeloma: a randomized phase 2 study. Blood 2014; 123:1826-1832). In an embodiment, pomalidomide is administered in a combination therapy with dexamethasone and an NTB-A directed antibody-drug conjugate of the present invention. In a further embodiment, pomalidomide is administered in a combination therapy with dexamethasone and a humanized 20F3 antibody-drug conjugate of the present invention. In a further embodiment, pomalidomide is administered in a combination therapy with dexamethasone and a h20F3ec-1910(2) of the present invention.

Pomalidomide has also been combined with carfilzomib and dexamethasone (see Shah J et al. Carfilzomib, pomalidomide, and dexamethasone (CPD) in patients with relapsed and/or refractory multiple myeloma. Blood 2015; 126: 2284-2290). In an embodiment, pomalidomide is administered in a combination therapy with carfilzomib, dexamethasone, and an NTB-A directed antibody-drug conjugate of the present invention. In a further embodiment, pomalidomide is administered in a combination therapy with carfilzomib, dexamethasone, and a humanized 20F3 antibody-drug conjugate of the present invention. In a further embodiment, pomalidomide is administered in a combination therapy with carfilzomib, dexamethasone, and a h20F3ec-1910(2) of the present invention.

Another exemplary agent for combination therapy is panobinostat (e.g. FARYDAK®), a histone deacetylase (HDAC) inhibitor used to treat cancer (including multiple myeloma) (see Wolf J L et al. A phase II study of oral panobinostat (LBH589) in adult patients with advanced refractory multiple myeloma. ASH Annual Meeting Abstracts, 2008). Panobinostat can be administered as a pill, capsule, or tablet for oral administration. In an embodiment, panobinostat is administered in a combination therapy with an NTB-A directed antibody-drug conjugate of the present invention. In a further embodiment, panobinostat is administered in a combination therapy with a humanized 20F3 antibody-drug conjugate of the present invention. In a further embodiment, panobinostat is administered in a combination therapy with a h20F3ec-1910(2) of the present invention.

Panobinostat can also be administered in a combination therapy with an NTB-A directed antibody-drug conjugate of the present invention and an additional agent. Panobinostat has been combined with various additional agents to treat multiple myeloma. For example, panobinostat has been combined with carfilzomib (see Berdeja J G et al.). In an embodiment, panobinostat is administered in a combination therapy with carfilzomib and an NTB-A directed antibody-drug conjugate of the present invention. In a further embodiment, panobinostat is administered in a combination therapy with carfilzomib and a humanized 20F3 antibody-drug conjugate of the present invention. In a further embodiment, panobinostat is administered in a combination therapy with carfilzomib and a h20F3ec-1910(2) of the present invention.

Panobinostat has also been combined with bortezomib and dexamethasone (see Richardson P et al. 2013). In an embodiment, panobinostat is administered in a combination therapy with bortezomib, dexamethasone, and an NTB-A directed antibody-drug conjugate of the present invention. In a further embodiment, panobinostat is administered in a combination therapy with bortezomib, dexamethasone, and a humanized 20F3 antibody-drug conjugate of the present invention. In a further embodiment, panobinostat is administered in a combination therapy with bortezomib, dexamethasone, and a h20F3ec-1910(2) of the present invention.

Another exemplary agent for combination therapy is ixazomib (NINLARO®), a proteasome inhibitor used to treat cancer (including multiple myeloma). Ixazomib can be administered orally. In an embodiment, ixazomib is administered in a combination therapy with an NTB-A directed antibody-drug conjugate of the present invention. In a further embodiment, ixazomib is administered in a combination therapy with a humanized 20F3 antibody-drug conjugate of the present invention. In a further embodiment, ixazomib is administered in a combination therapy with a h20F3ec-1910 (2) of the present invention.

Ixazomib can also be administered in a combination therapy with an NTB-A directed antibody-drug conjugate of the present invention and an additional agent. Ixazomib has been combined with various additional agents to treat multiple myeloma. For example, ixazomib has been combined with lenalidomide and dexamethasone (see Moreau P et al. Ixazomib, an investigational oral proteasome inhibitor, in combination with lenalidomide and dexamethasone, significantly extends progression-free survival for patients with relapsed and/or refractory multiple myeloma: the phase 3 tourmaline-MM1 study. ASH Annual Meeting Abstracts, 2015). In an embodiment, ixazomib is administered in a combination therapy with lenalidomide, dexamethasone, and an NTB-A directed antibody-drug conjugate of the present invention. In a further embodiment, ixazomib is administered in a combination therapy with lenalidomide, dexamethasone, and a humanized 20F3 antibody-drug conjugate of the present invention. In a further embodiment, ixazomib is administered in a combination therapy with lenalidomide, dexamethasone, and a h20F3ec-1910(2) of the present invention.

Other exemplary agents for combination therapy (particularly in the treatment of non-Hodgkin's lymphoma) include anti-CD20 antibodies (including rituximab, Ibritumomab tiuxetan, tositumomab, ofatumumab, veltuzumab, and obinutuzumab), anti-CD52 antibodies (including alemtuzumab), anti-PD1 antibodies (including nivolumab, pidilizumab, and pembrolizumab), anti-PDL1 antibodies (including durvulamab and atezolizumab), brentuximab vedotin, bendamustine, and bortezomib. In an embodiment, one of an anti-CD20 antibody, an anti-CD52 antibody, an anti-PD1 antibody, an anti-PDL1 antibody, brentuximab vedotin, bendamustine, and bortezomib is administered in a combination therapy with an NTB-A directed antibody-drug conjugate of the present invention. In a further embodiment, one of an anti-CD20 antibody, an anti-CD52 antibody, an anti-PD1 antibody, an anti-PDL1 antibody, brentuximab vedotin, bendamustine, and bortezomib is administered in a combination therapy with humanized 20F3 antibody-drug conjugate of the present invention. In a further embodiment, one of an anti-CD20 antibody, an anti-CD52 antibody, an anti-PD1 antibody, an anti-PDL1 antibody, brentuximab vedotin, bendamustine, and bortezomib is administered in a combination therapy with a h20F3ec-1910(2) of the present invention.

Additionally, other agents for combination therapy include chemotherapeutic regimens such as CHOP (cyclophosphamide, doxorubicin, vincristine, and prednisone); CVP (cyclophosphamide, vincristine, and prednisone); RCVP (rituximab+CVP); RCHOP (rituximab+CHOP); RCHP (rituximab, cyclophosphamide, doxorubicin, and prednisone); RICE (Rituximab+ifosamide, carboplatin, etoposide); RDHAP, (Rituximab+dexamethasone, cytarabine, cisplatin); RESHAP (rituximab+etoposide, methylprednisolone, cytarabine, cisplatin); R-BENDA (rituximab and Bendamustine), RGDP (rituximab, gemcitabine, dexamethasone, cisplatin). In an embodiment, one of CHOP, CVP, RCVP, RCHOP, RCHP, RICE, RDHAP, RESHAP, R-BENDA, and RGDP is administered in a combination therapy with an NTB-A directed antibody-drug conjugate of the present invention. In a further embodiment, one of CHOP, CVP, RCVP, RCHOP, RCHP, RICE, RDHAP, RESHAP, R-BENDA, and RGDP is administered in a combination therapy with humanized 20F3 antibody-drug conjugate of the present invention. In a further embodiment, one of CHOP, CVP, RCVP, RCHOP, RCHP, RICE, RDHAP, RESHAP, R-BENDA, and RGDP is administered in a combination therapy with a h20F3ec-1910(2) of the present invention.

Anti-NTB-A antibodies, as naked antibodies, or as antibody drug conjugates are administered in an effective regimen meaning a dosage, route of administration and frequency of administration that delays the onset, reduces the severity, inhibits further deterioration, and/or ameliorates at least one sign or symptom of cancer. In some instances, therapeutic efficacy can be observed in an individual patient relative to historical controls or past experience in the same patient. In other instances, therapeutic efficacy can be demonstrated in a preclinical or clinical trial in a population of treated patients relative to a control population of untreated patients.

Exemplary dosages for an anti-NTB-A naked antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg.

Exemplary dosages for anti-NTBA antibody drug conjugates are 1.0 µg/kg to about 10 mg/kg, 1.0 µg/kg to about 5 mg/kg, 1.0 µg/kg to about 5 mg/kg, from about 1.0 µg/kg to about 1.0 mg/kg, from about 10 µg/kg to about 3 mg/kg, from about 10 µg/kg to about 2 mg/kg, from about 1.0 µg/kg to 1.0 mg/kg, or from about 1.0 µg/kg to 500.0 µg/kg or from about 0.0 µg/kg to 80.0, 100.0, or 200.0 µg/kg.

Exemplary dosages for NTB-A directed PBD conjugates are generally from about 1.0 µg/kg to 1.0 mg/kg, or from about 1.0 µg/kg to 500.0 µg/kg or from about 0.0 µg/kg to 80.0, 100.0, or 200.0 µg/kg, although alternate dosages are contemplated.

Administration is typically parenteral. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends, in part, on the nature of the disorder (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibody drug conjugates can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with naked antibodies or antibody drug conjugates disclosed herein can be combined with chemotherapy, radiation, stem cell treatment, surgery other treatments effective against the disorder being treated. Useful classes of other agents that can be administered with an anti-NTB-A antibody or antibody drug conjugate include, for example, antibodies to other receptors expressed on cancerous cells, antitubulin agents (e.g., auristatins), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with naked antibodies or the anti-NTB-A antibody drug conjugate, optionally in combination with any of the other agents or regimens described above alone or as an antibody drug conjugate, can increase the median progression-free survival or overall survival time of patients with an NTB-A-expressing cancer (e.g., multiple myeloma, AML, NHL), especially when relapsed or refractory, by at least 30% or 40% but preferably 50%, 60% to 70% or even 100% or longer, compared to the same treatment (e.g., chemotherapy) but without an anti-NTB-A antibody alone or as a conjugate. In addition or alternatively, treatment (e.g., standard chemotherapy) including the anti-NTB-A a conjugate can increase the complete response rate, partial response rate, or objective response rate (complete+partial) of patients with an NTB-A-expressing cancer by at least 30% or 40% but preferably 50%, 60% to 70% or even 100% compared to the same treatment (e.g., chemotherapy) but without the anti-NTB-A antibody.

Typically, in a clinical trial (e.g., a phase II, phase II/III or phase III trial), the aforementioned increases in median progression-free survival and/or response rate of the patients treated with standard therapy plus the anti-NTB-A antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

In other applications, the anti-NTB-A antibodies disclosed herein can be used for detecting NTB-A in the context of clinical diagnosis or treatment or in research. Expression of NTB-A on a cancer provides an indication that the cancer is amenable to treatment with the antibodies of the present invention. The antibodies can also be sold as research reagents for laboratory research in detecting cells bearing NTB-A and their response to various stimuli. In such uses, an anti-NTB-A antibody can be labeled with a fluorescent molecule, a spin-labeled molecule, an enzyme, or a radio-isotype, and can be provided in the form of kit with all the necessary reagents to perform the assay for NTB-A. The antibodies can also be used to purify NTB-A, e.g., by affinity chromatography.

All patent filings, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), or as otherwise known.

Example 1

Antibody Selection

Lymphocytes harvested from spleen and lymph nodes of NTB-A antibody producing mice were fused to myeloma cells. Fused cells were recovered overnight in hybridoma growth media. Following recovery, cells were spun down and then plated in semi-solid media. Hybridomas were incubated and IgG producing hybridoma clones were picked. The 20F3 antibody was one of the few antibodies that demonstrated potent cytotoxicity as an ADC and bound to cynomolgus NTB-A.

Example 2

Design of Humanized Antibodies

Humanized antibodies were derived from the murine 20F3 antibody. Five humanized heavy chains (HA-HE) and four humanized light chains (LA-LD) were made incorporating back mutations at different positions. In some instances, backmutations will match the murine germline, but in other cases it will not (as in the case with somatic mutations). Humanized heavy and light chains were paired. See, FIGS. 1 and 2 for the sequence alignments and Tables 1-4.

TABLE 1

Humanizing Mutations in 20F3 Heavy Chain Variants

| $V_H$ Variant | $V_H$ Exon Acceptor Sequence | Donor Framework Residues |
| --- | --- | --- |
| h$V_H$A | VH7-4-1 | None |
| h$V_H$B | VH7-4-1 | H2 and H73 |
| h$V_H$C | VH7-4-1 | H2, H44, H73 and H76 |
| h$V_H$D | VH7-4-1 | H2, H44, H46, H73, H76 |
| h$V_H$E | VH7-4-1 | H2, H38, H44, H46, H68, H73, H76, and H91 |

TABLE 2

Humanizing Mutations in 20F3 Light Chain Variants

| $V_L$ Variant | $V_L$ Exon Acceptor Sequence | Donor Framework Residues |
| --- | --- | --- |
| h$V_L$A | VK3-11 | None |
| h$V_L$B | VK3-11 | L46, L47, L71 |
| h$V_L$C | VK3-11 | L1, L5, L46, L47, L71 |
| h$V_L$D | VK3-11 | L1, L5, L21, L46, L47, L58, L71 |

TABLE 3

Specific Mutations in 20F3 Heavy Chain Variants

| Variant | H2 | H38 | H44 | H46 | H68 | H73 | H76 | H91 |
| --- | --- | --- | --- | --- | --- | --- | --- | --- |
| HA | V | R | G | E | V | T | S | Y |
| HB | I* | R | G | E | V | K* | S | Y |
| HC | I* | R | D* | E | V | K* | N* | Y |
| HD | I* | R | D* | K* | V | K* | N* | Y |
| HE | I* | K* | D* | K* | A* | K* | N* | F* |

*Mouse residues

TABLE 4

Specific Mutations in 20F3 Light Chain Variants

| Variant | L1 | L5 | L21 | L46 | L47 | L58 | L71 |
| --- | --- | --- | --- | --- | --- | --- | --- |
| LA | E | T | L | L | L | I | F |
| LB | E | T | L | P* | W* | I | Y* |
| LC | Q* | S* | L | P* | W* | I | Y* |
| LD | Q* | S* | M* | P* | W* | V* | Y* |

*Mouse residues

Example 3

EC50 and Kd Measurements

To determine EC50, 3-point dose titrations of the unlabeled humanized anti-human NTB-A antibodies were mixed with a constant concentration (5 nM final) of mouse 20F3 antibody conjugated to Alexa Fluor 647. Antigen positive Ramos cells were plated at $1\times10^5$ cells per well in a 96 well V-bottom plate (Thermo Scientific, Rochester, N.Y.). Fifty-fold serial dilutions of antibodies were prepared in FACs buffer (PBS+2% fetal bovine serum) and were added to the cells in duplicate. The antibody solutions were incubated with cells for 1 hour on ice, protected from light. The cells were washed twice with FACs buffer and analyzed on the LSRII flow cytometer (BD BioSciences, San Jose, Calif.). EC50 values were determined with GraphPad Prism software (La Jolla, Calif.). Results are shown in Table 5.

TABLE 5

EC50 Binding Determinations for different permutations of humanized heavy and light chains of humanized 20F3 compared with murine 20F3 EC50 (nM)

| | HA | HB | HC | HD | HE |
| --- | --- | --- | --- | --- | --- |
| LA | 147 | 71 | 25 | 15 | 31 |
| LB | 12 | 6 | 5 | 3 | 4 |
| LC | 27 | 12 | 8 | 6 | 10 |
| LD | 12 | 4 | 5 | 3 | 2 |

Murine 20F3 EC50 is 2 nM.

Dose titrations of the anti-human NTB-A antibodies conjugated to Alexa Fluor 647 (h20F3_HDLD-AF647) were used to generate saturation binding curves. Antigen positive Ramos cells were plated at $1\times10^5$ cells per well in a 96 well V-bottom plate (Thermo Scientific, Rochester, N.Y.). Three-fold serial dilutions of 2× concentrated antibodies were prepared in FACs buffer (PBS+2% fetal bovine serum) and were added to the cells in duplicate. The antibody solutions were incubated with cells for 1 hour on ice, protected from light. The cells were washed twice with FACs buffer and analyzed on the LSRII flow cytometer (BD BioSciences, San Jose, Calif.). KD values were determined with GraphPad Prism software (La Jolla, Calif.). Anti-human NTB-A antibodies h20F3_HDLD and chimeric 20F3 were tested for binding to 293-F17 cells overexpressing cynomolgus-NTB-A. 293-F17/cynomolgus-NTB-A cells were plated at $5\times10^5$ cells/well in FACS buffer (PBS+2% fetal bovine serum+ 0.02% azide) and incubated with 20 µg/mL antibody for 30 minutes on ice. The cells were washed twice and stained with 30 µg/mL goat anti-human IgG-PE (Jackson ImmunoResearch, West Grove, Pa.) for 30 minutes, on ice and protected from light. Cells were again washed twice with FACs buffer. Stained cells were analyzed on the FACs Calibur flow cytometer (BD BioSciences, San Jose, Calif.). Results are shown in Table 6.

TABLE 6

Saturation Binding for humanized 20F3 variant
HDLD antibody compared with chimeric 20F3.

| Antibody | Ramos Kd (nM) | Cyno binding |
|---|---|---|
| chimeric | 1.68 | positive |
| HDLD | 2.2 | positive |

Example 4

Effector Function

Complement-Dependent Cytotoxicity (CDC): Normal human T cells (All Cells, Alameda, Calif.) or cancer cell lines (ATCC, Manassas, Va.) were labeled with 5 µM Sytox Green (Life Technologies, Grand Island, N.Y.), then bound with serial a serial dose titrations of anti-human NTB-A h20F3 antibody or PBD dimer ADCies (0.02-50 µg/mL) in RPMI1640 media+1020% human serum (Complement Technology, Tyler, Tex. or Solomon Park Research Laboratories, Kirkland, Wash. Cells were incubated at 37° C., 5% CO2 for 2 hours, and fluorescence from lysed cells was measured with an Envision plate reader (Perkin Elmer, Waltham, Mass.). Data was expressed as a percentage of maximum cell lysis determined with a positive control of 1% TritonX-100-treated cells (Sigma, ST. Louis, Mo.).

Three cell types were used for analysis: normal human T cells, WIL2-S cells, and Raji cells. Expression of relevant receptors on each cell type is found in Table 7 and is indicated as number of receptor per cell.

TABLE 7

Expression of receptors

| Cell Type | NTB-A | CD52 | CD20 |
|---|---|---|---|
| T cell | 6,900 | 115,200 | 0 |
| WIL2S | 19,900 | 34,200 | 502,700 |
| Raji | 39,900 | 29,200 | 394,100 |

As can be seen from Table 8 below, the humanized 20F3-HDLDwt IgG1 antibody and the ec variant (antibodies with cysteine at the 239 position carry the designation ec) have no CDC activity against normal resting T lymphocytes, WIL2-S and Raji cell lines. Similar results were observed for the h20F3ec-1910(2) ADC.

TABLE 8

CDC activity for humanized 20F3 antibodies and
ADC as compared to Campath and Rituximab Maximum % Specific Cell Lysis

| Cell Type | h20F3wt | h20F3ec | h20F3ec-1910(2) | Campath (CD52) | Rituximab (CD20) |
|---|---|---|---|---|---|
| Normal human T cells | 1.3 ± 2.8 | 2.2 ± 1.8 | 2.1 ± 3.0 | 108 ± 5.2 | Not tested |
| WIL2-S cell line | 0.0 ± 0.0 | 0.14 ± 0.2 | 0.3 ± 0.0 | Not tested | 66 ± 1.4 |
| Raji cell line | 2.1 ± 0.6 | 3.3 ± 0.7 | 0.0 ± 0.0 | Not tested | 45 ± 5.7 |

Antibody-Dependent Cellular Cytotoxicity (ADCC) Activity Assay: ADCC cytotoxic activity was measured by chromium-51 release in which effector natural killer (NK) cells kill (lyse) target cells via binding to the antibody or ADC on the target cells. WIL2-S cells were labeled with chromium-51, bound with antibody (0.1 ng/mL-10 µg/mL), and then incubated with NK cells at an effector to target ratio of 10:1 for 4 hours at 37° C., 5% $CO_2$. Supernatant was removed to a filter plate and chromium-51 counts were measured with a TopCount (Perkin Elmer, Waltham, Mass.). Data was expressed as a percentage of maximum specific cell lysis determined with a positive control of 1% TritonX-100-treated cells (Sigma, St. Louis, Mo.).

A flow cytometry-based assay was used to measure ADCC activity on normal human T cells. PKH2-labeled normal human T cell targets were bound with titrations of antibody (0.1 ng/mL-10 µg/mL) and then incubated with effector NK cells at an effector to target ratio of 10:1 for 4 hours at 37° C., 5% $CO_2$. Viability was determined by 7-AAD incorporation as measured on the FACsCalibur flow cytometer (BD BioSciences, San Jose, Calif.).

As can be seen from Table 9 below, the humanized 20F3-HDLDwt antibody and the ec variant have low to moderate ADCC activity. The h20F3ec-1910(2) PBD dimer ADC exhibited reduced ADCC activity relative to unconjugated h20F3ec antibody. Receptor numbers are disclosed in Table 7.

TABLE 9

ADCC activity for humanized 20F3 as
compared to Campath and Rituximab

Maximum % Specific Cell Lysis

| Cell Type | h20F3wt IgG1 | h20F3ec | h20F3ec-1910(2) | Campath (CD52) | Rituximab (CD20) |
|---|---|---|---|---|---|
| Normal human T cells | 38 ± 0.8 | 40 ± 0.6 | 19 ± 1.0 | 60 ± 3.5 | Not tested |
| WIL2-S cell line | 21 ± 0.6 | 25 ± 2.4 | 16 ± 3.3 | Not tested | 42 ± 6.0 |

To assess NTB-A mediated ADCP activity, normal T lymphocytes or tumor cells were labeled with the red fluorescent membrane dye, PKH26, then labeled with antibody or ADC in a 5-point, 10-fold dilution series starting at 2 µg/mL. Cells were then incubated for 30 minutes on ice and washed twice with PBS. Cells were mixed with monocyte-derived macrophages for one hour at 37° C. The cell mixture was then stained with Alexa Fluor 488-conjugated murine anti-CD11b to label macrophages and analyzed by flow cytometry to detect PKH26+CD11b+ double-labeled fluorescent cells. Phagocytic activity was calculated as (percent PKH26+CD11b+)/(percent CD11b+ cells) multiplied by one hundred.

As can be seen from Table 10 below, the humanized 20F3-HDLDwt antibody and the ec variant have ADCP activity moderately lower than rituximab and campath antibody controls on cancer cell lines. Similar results were observed for the h20F3ec-1910(2) ADC.

TABLE 10

ADCP activity for humanized 20F3 as
compared to Campath and Rituximab

| | Maximum % Phagocytosis | | | | |
|---|---|---|---|---|---|
| Cell Type | h20F3wt IgG1 | h20F3ec | h20F3ec-1910(2) | Campath (CD52) | Rituximab (CD20) |
| Normal human T cells | 42 | 33 | 37 | 57 | Not tested |
| WIL2-S cell line | 45 | 45 | 45 | Not tested | 56 |
| Raji cell line | 48 | 44 | 45 | Not tested | 57 |

Example 5

ADC Internalization

Multiple myeloma cell lines (MM.1R or U-266) were bound with saturating concentrations of ADC (10 μg/mL), washed with media, and incubated at either 37° C. or 4° C. Time points were collected at which samples were stained with PE-labeled goat-anti-human antibody (Jackson ImmunoResearch, West Grove, Pa.) and fixed in 1% PFA/PBS. Once all time points were collected, the mean fluorescence intensity was measured on the FACs Calibur flow cytometer (BD BioSciences, San Jose, Calif.). The anti-NTB-A h20F3ec-1910(2) PBD dimer ADC rapidly internalized into MM.1R cells, with 80% of the ADC internalized within 4 hours at 37° C. incubation. Only 20% of h20F3ec-1910(2) ADC was internalized at 4 hours when cells were kept at 4° C. control condition.

Cell surface and intracellular localization of ADC in MM.1R cells were also detected with a mouse anti-idiotypic antibody specific to the h20F3ec antibody. The ADC was allowed to bind MM.1R cells for 30 minutes at 4° C., and the ADC was found to rapidly internalize to lysosomes.

Example 6

Cytotoxicity of ADCs on MM Cancer Cell Lines

Humanized antibodies (HDLD) were tested as PBD and auristatin antibody drug conjugates. The antimitotic agent monomethyl auristatin E (MMAE) was conjugated to anti-NTB-A mAbs via a cathepsin-cleavable valine-citrulline (vc) linker. A second auristatin, Auristatin-2 was conjugated to anti-NTB-A mAbs via a peptide linker. For the PBD conjugates, the drug-linker SGD-1910 was conjugated to the anti-NTBA antibody via a thiol group of a cysteine residue introduced at position 239 of the IgG1 chain of the antibody (numbering according to the EU Index) and the average drug load was about 2 drugs per antibody. Antibodies with cysteine at the 239 position carry the designation ec. Preparation was as described in WO2011/130613 using the anti-NTBA antibodies described herein. The ADCs were serially diluted 3-fold in media to produce a 10 point dose curve (1,000 ng/mL-0.05081 ng/mL) and applied to multiple myeloma cells cultured in 96-well assay plates. The cell lines were treated with anti-NTB-A ADCs in quadruplicate and incubated for 96 hours at 37° C., 5% CO2. Cells were assayed for viability using the Cell Titer Glo luminescent cytotoxicity assay (Promega), and data collected using an EnVision plate reader (Perkin Elmer). Dose effect curves and IC50 values were calculated using GraphPad Prism software. The results are shown in Tables 11 and 12.

The mechanism of action on MM.1R cells was also analyzed. MM.1R cells were treated with ADC, and activation of ATR and ATM kinases was quantitated by western blotting with phospho-epitope specific antibodies. The ADC activated ATM/ATR levels nearly equivalent to free PBD dimer drug, thus the ADC activates the DNA damage response in MM cells.

TABLE 11

IC50 values of various antibody drug conjugates with humanized 20F3 in
multiple myeloma cell lines (IC50 values in ng/mL; hIgG is a
non-binding negative control antibody)

| | | | Multiple Myeloma Cell Lines (# NTB-A receptors/cell) | | | | |
|---|---|---|---|---|---|---|---|
| Antibody | Drug Linker | Drug Load | EJM (9800) | MM.1R MM.1S (21000) | (14800) | U-266 (18300) | LP-1 (0) |
| h20F3 | vcMMAE | 4 | 162 | 696 | >1000 | 22 | >1000 |
| h20F3 | Auristatin-2 | 8 | 22 | 6 | 7 | 4 | >1000 |
| h20F3ec | PBD dimer | 2 | >1000 | 1 | 1 | 8 | >1000 |
| hIgG | vcMMAE | 4 | >1000 | >1000 | >1000 | >1000 | >1000 |
| hIgG | Auristatin-2 | 8 | >1000 | >1000 | >1000 | >1000 | >1000 |
| hIgG | PBD dimer | 2 | >1000 | >1000 | >1000 | >1000 | >1000 |

TABLE 12

IC50 values of various antibody drug conjugates with humanized 20F3 in
NHL and AML cell lines (IC50 values in ng/mL; hIgG is a non-binding
negative control antibody)

| | | | NHL and AML Cell Lines (# NTB-A receptors/cell) | | | |
|---|---|---|---|---|---|---|
| Antibody | Drug Linker | Drug Load | Ramos (24500) | CA46 (15,000) | HEL92.1.7 (10200) | HNT-34 (57300) |
| h20F3 | vcMMAE | 4 | 11 | 44 | >1000 | 19 |
| h20F3 | Auristatin-2 | 8 | 2 | 3 | 455 | 2 |

TABLE 12-continued

IC50 values of various antibody drug conjugates with humanized 20F3 in NHL and AML cell lines (IC50 values in ng/mL; hIgG is a non-binding negative control antibody)

| Antibody | Drug Linker | Drug Load | NHL and AML Cell Lines (# NTB-A receptors/cell) | | | |
|---|---|---|---|---|---|---|
| | | | Ramos (24500) | CA46 (15,000) | HEL92.1.7 (10200) | HNT-34 (57300) |
| h20F3ec | PBD dimer | 2 | 0.8 | 0.9 | 2 | 0.5 |
| hIgG | vcMMAE | 4 | >1000 | >1000 | >1000 | >1000 |
| hIgG | Auristatin-2 | 8 | >1000 | >1000 | >1000 | >1000 |
| hIgGec | PBD dimer | 2 | >1000 | >1000 | >1000 | >1000 |

Example 7

Cytotoxicity of ADCs on Human Lymphocytes

To assess the cytotoxic effects of anti-NTB-A ADCs on resting human T and B lymphocytes, purified cells were seeded into black 96-well assay plates. Cells were then treated with anti-NTB-A ADCs starting at 10 µg/mL titrated down 5-fold for a total of 8 dilution points. For free drug treatment, cells were dosed with either MMAE starting at 1,000 nM or free PBD dimer starting at 100 nM titrated down 5-fold for a total of 8 dilution points. Plates were incubated at 37° C., 5% $CO_2$ for 96 hours then allowed to equilibrate to room temperature. An equal volume of Cell-Titer Glo reagent was added to each well and the plate was incubated an additional 30 minutes at room temperature. Plates were then read on a Perkin Elmer Envision plate reader. Dose effect curves and IC50 values were calculated using GraphPad Prism software. The results are shown in Table 13.

TABLE 13

IC50 values of chimeric 20F3 antibody and free drug on resting human T and B lymphocytes.

| Donor | Cell Type | NTB-A (receptor #) | c20F3-1910(2) (ng/mL) | c20F3-vcMMAE(4) (ng/mL) | Free MMAE (nM) | Free PBD dimer (nM) |
|---|---|---|---|---|---|---|
| 1 | B cell | 6,811 | 1,468 | >10,000 | 3 | 1 |
| 2 | B cell | 11,037 | 1,270 | >10,000 | 2 | 1 |
| 3 | B cell | 8,771 | 3,421 | >10,000 | 5 | 3 |
| 4 | T cell | 5,547 | >10,000 | >10,000 | >1000 | 28 |
| 5 | T cell | 7,979 | >10,000 | >10,000 | >1000 | 25 |
| 6 | T cell | 5,522 | >10,000 | >10,000 | >1000 | 27 |

Resting human T lymphocytes were not affected by PBD dimer or auristatin chimeric 20F3 ADCs in a 96 hour cytotoxicity assay. Free PBD dimer was cytotoxic to resting T lymphocytes, indicating they are sensitive to this DNA damage drug. Therefore, cell surface levels of NTB-A are too low for the c20F3-1910(2) ADC to internalize enough PBD drug to kill resting T lymphocytes. In contrast, neither MMAE free drug nor c20F3-vcMMAE(4) ADC were potent on resting T lymphocytes. Resting human B lymphocytes are sensitive to both free drug MMAE and PBD dimer. However, c20F3-1910(2) ADC had a cytotoxic effect on resting B lymphocytes only at high ADC concentrations (>1,000 ng/mL), while c20F3-vcMMAE(4) ADC had no cytotoxic effect. Therefore, cell surface levels of NTB-A are too low on B lymphocytes to mediate a potent cytotoxic effect with either PBD dimer or auristatin c20F3 ADCs.

Example 8

In Vivo MM Xenograft Studies

NSG (NOD scid gamma; NOD.Cg-Prkdc$^{scid}$ Il2rg$^{tm1wjl}$/SzJ) mice were implanted with 1 million MM.1R cells, per animal intravenously to generate a disseminated model of multiple myeloma. Five days after tumor cell implant, n=10 mice per treatment group were given a single intraperitoneal injection of h20F3ec-1910(2) PBD ADC or non-binding control hIgGec-1910(2) PBD ADC. PBD ADC dose levels examined were 333 µg/kg, 111 µg/kg, and 37 µg/kg. Mice with advanced tumor burden were sacrificed upon showing symptoms of hind limb paralysis, cranial swelling, and/or moribundity. As shown in FIG. 3, the HDLD h20F3ec-1910(2) PBD dimer ADCs produced durable complete responses in 10/10 mice at all dose levels (single dose), while non-binding control PBD ADC dosed mice were all sacrificed due to disease by day-80 of the study. A statistically significant difference (P<0.0001 Mantel-Cox test) between h20F3ec-1910(2) ADC (37 µg/kg) versus control hIgGec-1910(2) ADC (333 µg/kg) groups was achieved.

Figure 4:
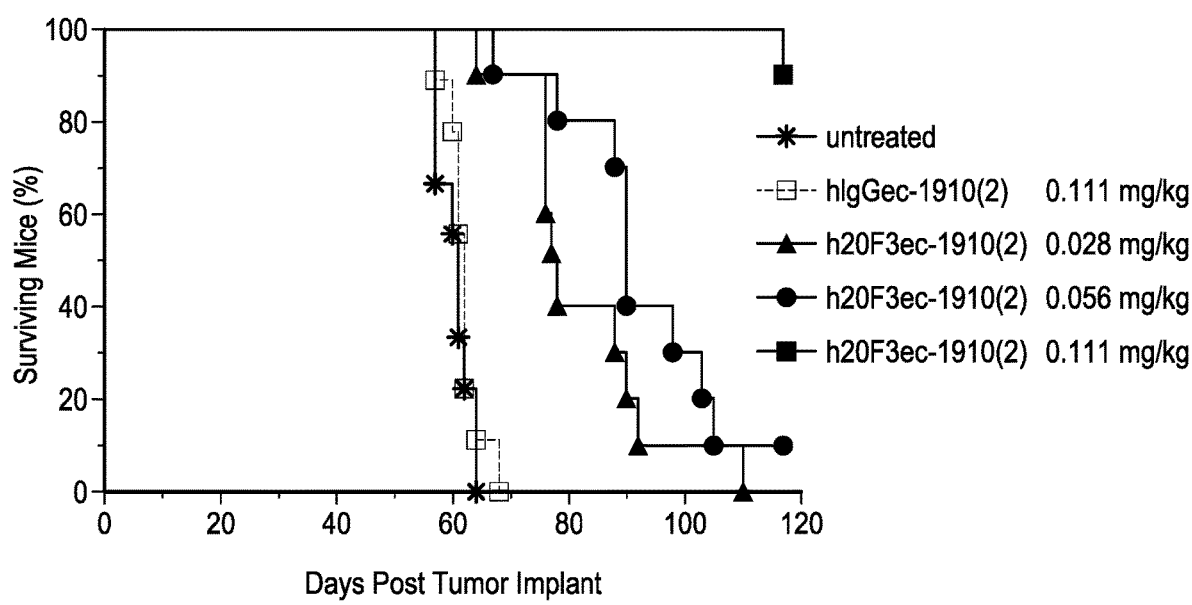
FIG. 4 shows the results of a multiple myeloma disseminated xenograft study in the U-266 cell line in NSG mice. The dose is indicated on the figure. The ADC is a humanized 20F3 PBD antibody drug conjugate

NSG (NOD scid gamma; NOD.Cg-Prkdc$^{scid}$ Il2rg$^{tm1wjl}$/SzJ) mice were implanted with 5 million U-266 cells per animal intravenously to generate a disseminated model of multiple myeloma. Five days after tumor cell implant, n=10 mice per treatment group were given a single intraperitoneal injection of h20F3ec-1910(2) PBD ADC or non-binding control hIgGec-1910(2) PBD ADC. PBD ADC dose levels examined were 111 µg/kg, 56 µg/kg, and 28 µg/kg. Mice with advanced tumor burden were sacrificed upon showing symptoms of hind limb paralysis, cranial swelling, and/or moribundity. As shown in FIG. 4, the HDLD h20F3ec-1910(2) PBD dimer ADCs produced durable complete responses in 9/10 mice at 111 µg/kg (single dose). At lower dose levels (28 and 56 µg/kg) h20F3ec-1910(2) produced significant (P<0.0001 Mantel-Cox test) delay of disease onset versus hIgGec-1910(2) (111 µg/kg) control PBD ADC.

Figure 5:
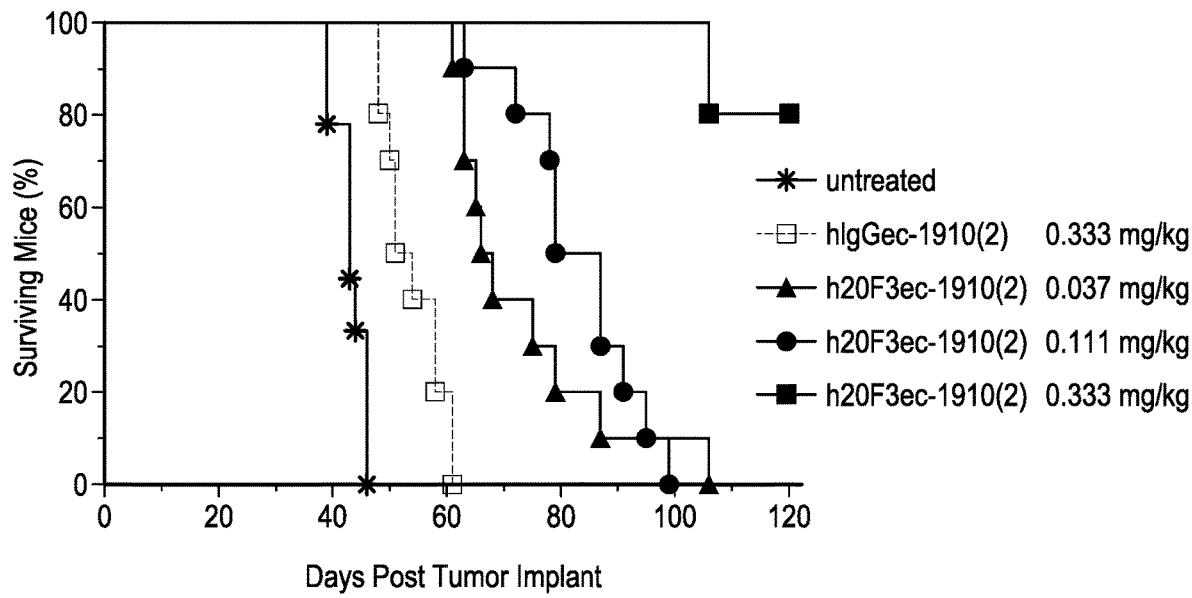
FIG. 5 shows the results of a multiple myeloma disseminated xenograft study in the EJM cell line in NSG mice. The dose is indicated on the figure. The ADC is a humanized 20F3 PBD antibody drug conjugate

NSG (NOD scid gamma; NOD.Cg-Prkdc$^{scid}$ Il2rg$^{tm1wjl}$/SzJ) mice were implanted with 10 million EJM cells per animal intravenously to generate a disseminated model of multiple myeloma. Five days after tumor cell implant, n=10 mice per treatment group were given a single intraperitoneal injection of h20F3ec-1910(2) PBD ADC or non-binding control hIgGec-1910(2) PBD ADC. PBD ADC dose levels examined were 333 µg/kg, 111 µg/kg, and 37 µg/kg. Mice with advanced tumor burden were sacrificed upon showing symptoms of hind limb paralysis, cranial swelling, and/or moribundity. As shown in FIG. 5, the HDLD h20F3ec-1910(2) PBD dimer ADCs produced durable complete responses in 8/10 mice at 333 µg/kg (single dose). At lower dose levels (37 and 111 µg/kg) h20F3ec-1910(2) produced significant (P<0.0001 Mantel-Cox test) delay of disease onset versus hIgGec-1910(2) (333 µg/kg) control PBD ADC.

Figure 6:
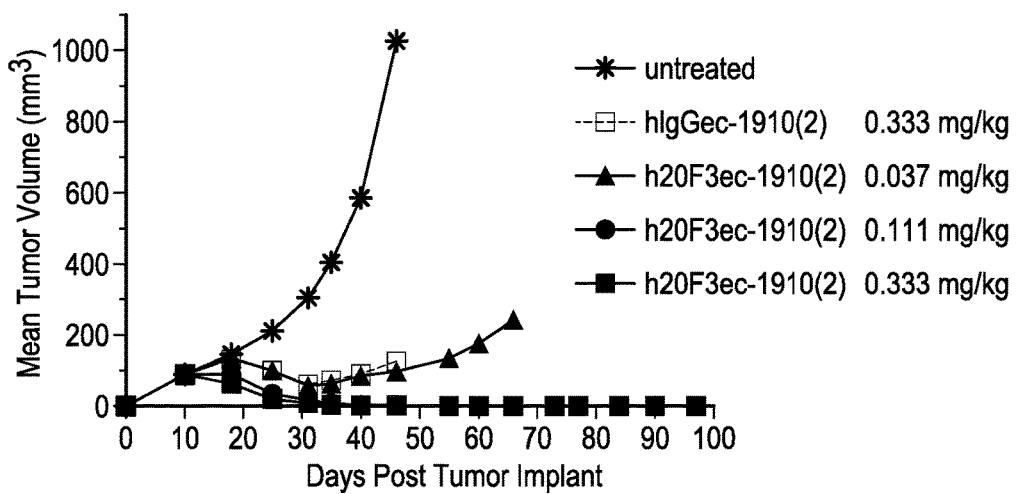
FIG. 6 shows the results of an AML subcutaneous xenograft study in the HNT-34 cell line in SKID mice. The dose is indicated on the figure. The ADC is a humanized 20F3 PBD antibody drug conjugate

SCID (C.B-17/Sz-Prkdc$^{scid}$) mice were implanted with 5 million HNT-34 acute myeloid leukemia cells per animal subcutaneously. When mean tumor volume reached 100 mm$^3$, n=10 mice per treatment group were given a single intraperitoneal injection of h20F3ec-1910(2) PBD ADC or non-binding control hIgGec-1910(2) PBD ADC. PBD ADC dose levels examined were 333 µg/kg, 111 µg/kg, and 37 µg/kg. Individual mice were sacrificed when subcutaneous HNT-34 tumor volume reached 1,000 mm$^3$. As shown in FIG. 6, the HDLD h20F3ec-1910(2) PBD dimer ADCs produced durable complete responses in all mice at the 333 µg/kg and 111 µg/kg dose levels. At the lower dose level of 37 µg/kg, h20F3ec-1910(2) produced a strong tumor delay and 2/10 durable complete responses. The hIgGec-1910(2) control PBD ADC produced 0/10 complete responses at 333 µg/kg.

Figure 7:
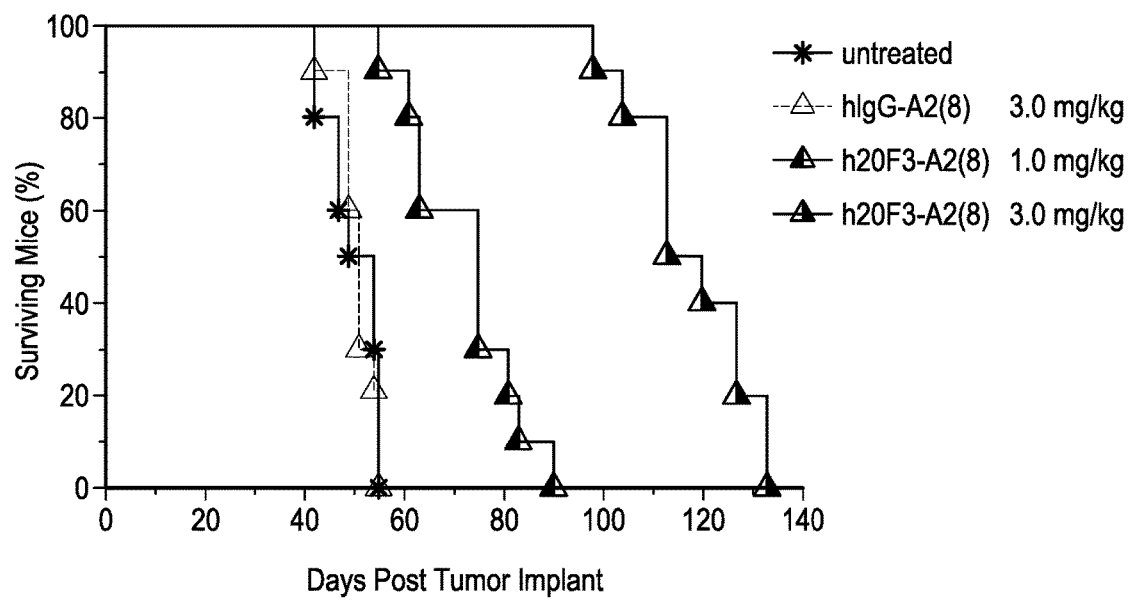
FIG. 7 shows the results of a multiple myeloma disseminated xenograft study in the MM.1R cell line in NSG mice. The dose is indicated on the figure. The ADC is a humanized 20F3 auristatin antibody drug conjugate.

NSG (NOD scid gamma; NOD.Cg-Prkdc$^{scid}$ Il2rg$^{tm1wjl}$/SzJ) mice were implanted with 1 million MM.1R cells per animal intravenously to generate a disseminated model of multiple myeloma. Five days after tumor cell implant, n=10 mice per treatment group were given a single intraperitoneal injection of h20F3-Auristatin2(8) ADC or non-binding control hIgG-Auristatin2(8) ADC. Auristatin2 ADC dose levels examined were 3.0 mg/kg and 1.0 mg/kg. Mice with advanced tumor burden were sacrificed upon showing symptoms of hind limb paralysis, cranial swelling, and/or moribundity. As shown in FIG. 7, the HDLD h20F3-Auristatin2(8) ADC produced a significant tumor delay (P<0.0001 Mantel-Cox test) at 3.0 mg/kg and 1.0 mg/kg dose levels versus control hIgG-Auristatin2(8) ADC (3.0 mg/kg) in the disseminated MM.1R model.

Figure 8:
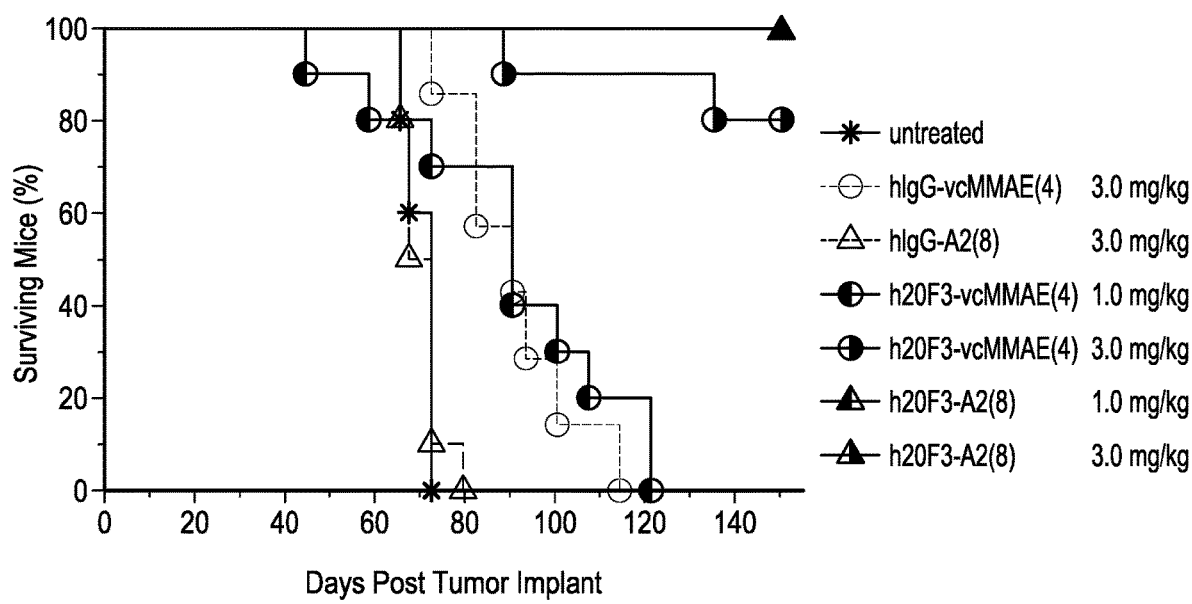
FIG. 8 shows the results of a multiple myeloma disseminated xenograft study in the U-266 cell line in NSG mice. The dose is indicated on the figure. The ADCs are both humanized 20F3 auristatin antibody drug conjugates.

NSG (NOD scid gamma; NOD.Cg-Prkdc$^{scid}$ Il2rg$^{tm1wjl}$/SzJ) mice were implanted with 5 million U-266 cells per animal intravenously to generate a disseminated model of multiple myeloma. Five days after tumor cell implant, n=10 mice per treatment group were given a single intraperitoneal injection of either anti-NTB-A ADCs h20F3-vcMMAE(4), h20F3-Auristatin2(8), or non-binding control ADCs hIgG-vcMMAE(4) and hIgG-Auristatin2(8). ADC dose levels examined were 3.0 mg/kg, and 1.0 mg/kg. Mice with advanced tumor burden were sacrificed upon showing symptoms of hind limb paralysis, cranial swelling, and/or moribundity. As shown in FIG. 8, the h20F3-vcMMAE(4) ADC produced durable complete responses in 8/10 mice at 3.0 mg/kg dose level. The h20F3-Auristatin2(8) ADC produced 10/10 durable complete responses at both the 1.0 mg/kg and 3.0 mg/kg dose levels. The anti-NTB-A Auristatin2 ADCs had greater antitumor activity than the vcMMAE(4) ADCs, especially at the 1.0 mg/kg dose level.

Figure 9:
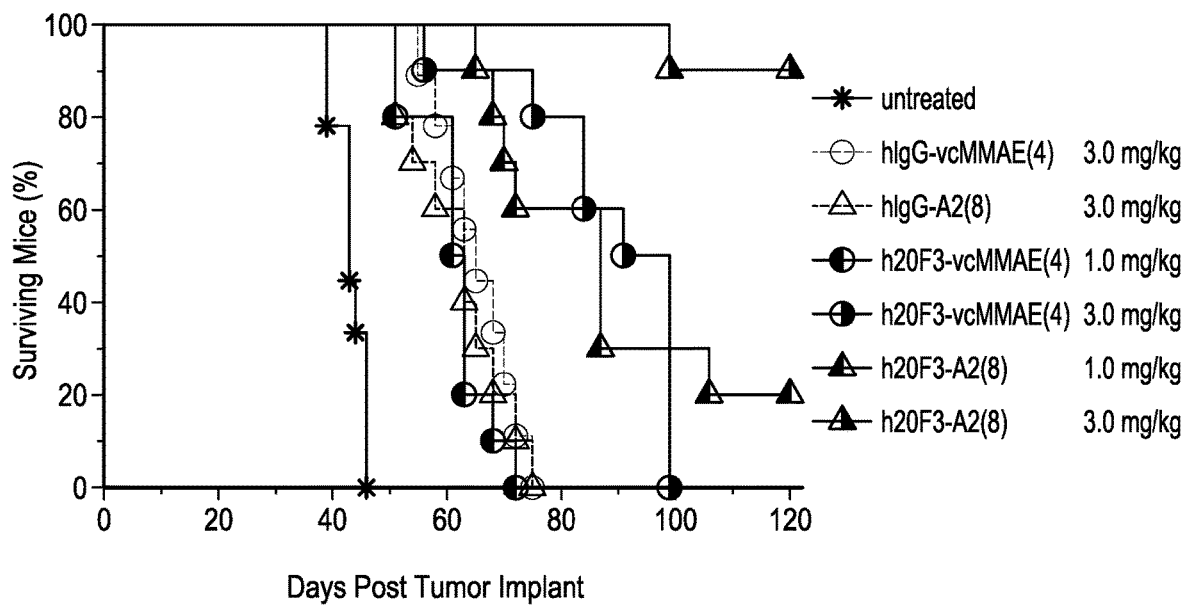
FIG. 9 shows the results of a multiple myeloma disseminated xenograft study in the EJM cell line in NSG mice. The dose is indicated on the figure. The ADCs are both humanized 20F3 auristatin antibody drug conjugates.

NSG (NOD scid gamma; NOD.Cg-Prkdc$^{scid}$ Il2rg$^{tm1wjl}$/SzJ) mice were implanted with 10 million EJM cells per animal intravenously to generate a disseminated model of multiple myeloma. Five days after tumor cell implant, n=10 mice per treatment group were given a single intraperitoneal injection of either anti-NTB-A ADCs h20F3-vcMMAE(4), h20F3-Auristatin2(8), or non-binding control ADCs hIgG-vcMMAE(4) and hIgG-Auristatin2(8). ADC dose levels examined were 3.0 mg/kg, and 1.0 mg/kg. Mice with advanced tumor burden were sacrificed upon showing symptoms of hind limb paralysis, cranial swelling, and/or moribundity. As shown in FIG. 9, the HDLD h20F3-vcMMAE(4) ADC produced a significant (P=0.0002 Mantel-Cox test) tumor delay versus hIgG-vcMMAE(4) control ADC at the 3.0 mg/kg dose level. The h20F3-Auristatin2(8) ADC produced 2/10 or 9/10 durable complete responses at the 1.0 mg/kg and 3.0 mg/kg dose levels, respectively. The anti-NTB-A Auristatin2 ADCs had significantly greater antitumor activity than the vcMMAE(4) ADCs at 1.0 mg/kg (P=0.0002 Mantel-Cox test) and 3.0 mg/kg (P<0.0001 Mantel-Cox test) dose levels.

Figure 10:
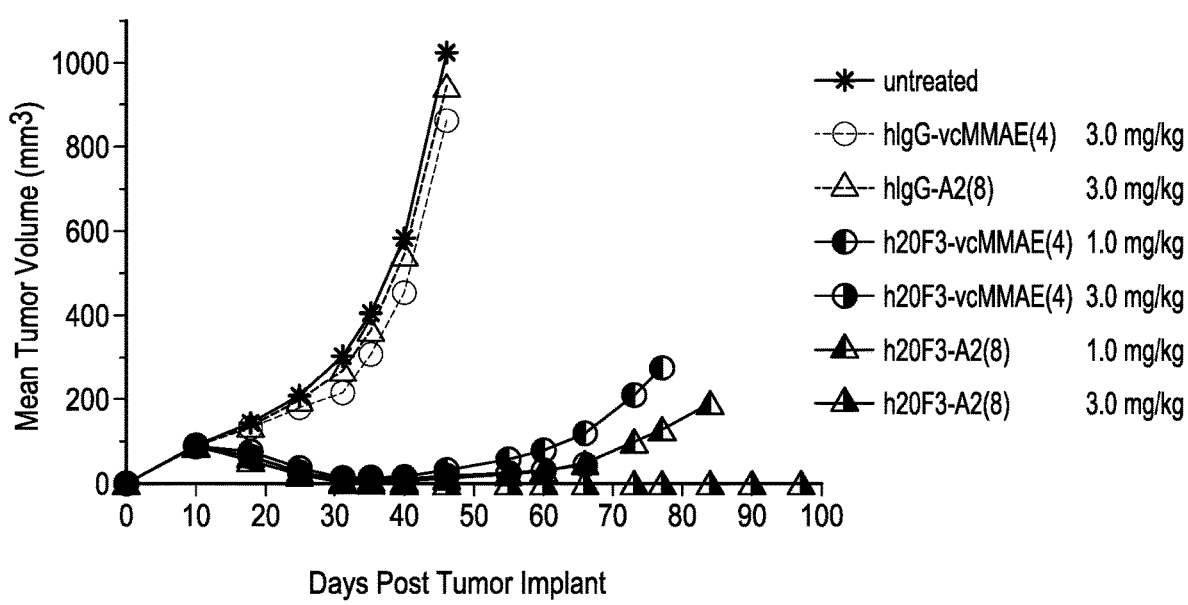
FIG. 10 shows the results of an AML subcutaneous xenograft study in the HNT-34 cell line in SKID mice. The dose is indicated on the figure. The ADCs are both humanized 20F3 auristatin antibody drug conjugates.

SCID (C.B-17/Sz-Prkdc$^{scid}$) mice were implanted with 5 million HNT-34 acute myeloid leukemia cells per animal subcutaneously. When mean tumor volume reached 100 mm$^3$, n=10 mice per treatment group were given a single intraperitoneal injection of either anti-NTB-A ADCs h20F3-vcMMAE(4), h20F3-Auristatin2(8), or non-binding control ADCs hIgG-vcMMAE(4) and hIgG-Auristatin2(8). ADC dose levels examined were 3.0 mg/kg, and 1.0 mg/kg. Individual mice were sacrificed when subcutaneous HNT-34 tumor volume reached 1,000 mm$^3$. As shown in FIG. 10, both the vcMMAE(4) and Auristatin2(8) HDLD h20F3 ADCs were very active in the HNT-34 subcutaneous AML model. The h20F3-vcMMAE(4) ADC produced durable complete responses in 4/10 or 9/10 mice at 1.0 mg/kg or 3.0 mg/kg dose levels, respectively. The h20F3-Auristatin2(8) ADC produced 3/10 or 9/10 durable complete responses at 1.0 mg/kg or 3.0 mg/kg dose levels, respectively.

Example 9

In Vivo Non-Hodgkin Lymphoma Xenograft Studies

Figure 11:
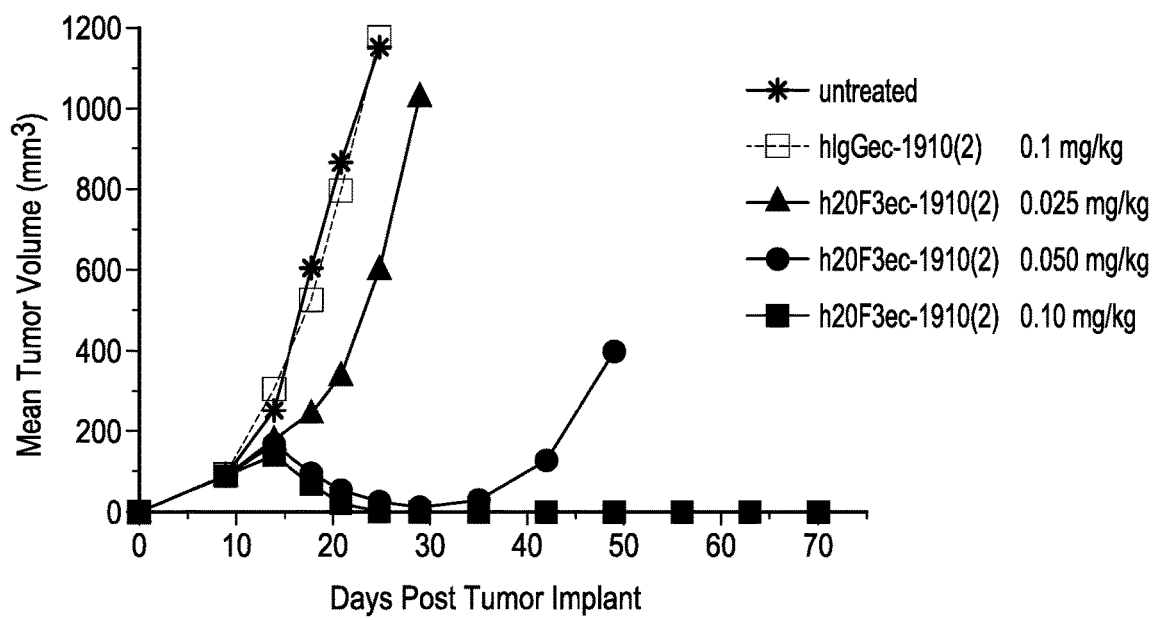
FIG. 11 shows the results of a non-Hodgkin lymphoma subcutaneous xenograft study in the Raji cell line in SCID mice. The dose is indicated on the figure. The ADCs are both humanized 20F3 auristatin antibody drug conjugates.

SCID (C.B-17/Sz-Prkdc$^{scid}$) mice were implanted with 5 million Raji non-Hodgkin lymphoma cells per animal subcutaneously. When mean tumor volume reached 100 mm$^3$, n=6 mice per treatment group were given a single intraperitoneal injection of h20F3ec-1910(2) PBD ADC or control hIgGec-1910(2) PBD ADC. PBD ADC dose levels examined were 100 ug/kg, 50 ug/kg, and 25 ug/kg. Individual mice were sacrificed when subcutaneous Raji tumor volume reached 1,000 mm$^3$. As shown in FIG. 11, the HDLD h20F3ec-1910(2) PBD dimer ADCs produced durable complete responses in all mice at the 100 ug/kg dose level. In addition, h20F3ec-1910(2) PBD ADC produced durable complete responses in 4/6 mice at 50 ug/kg dose level, while tumor growth delay was observed at the 25 ug/kg dose level. The hIgGec-1910(2) control PBD ADC had no antitumor activity at 100 ug/kg and produced 0/6 complete responses.

Figure 12:
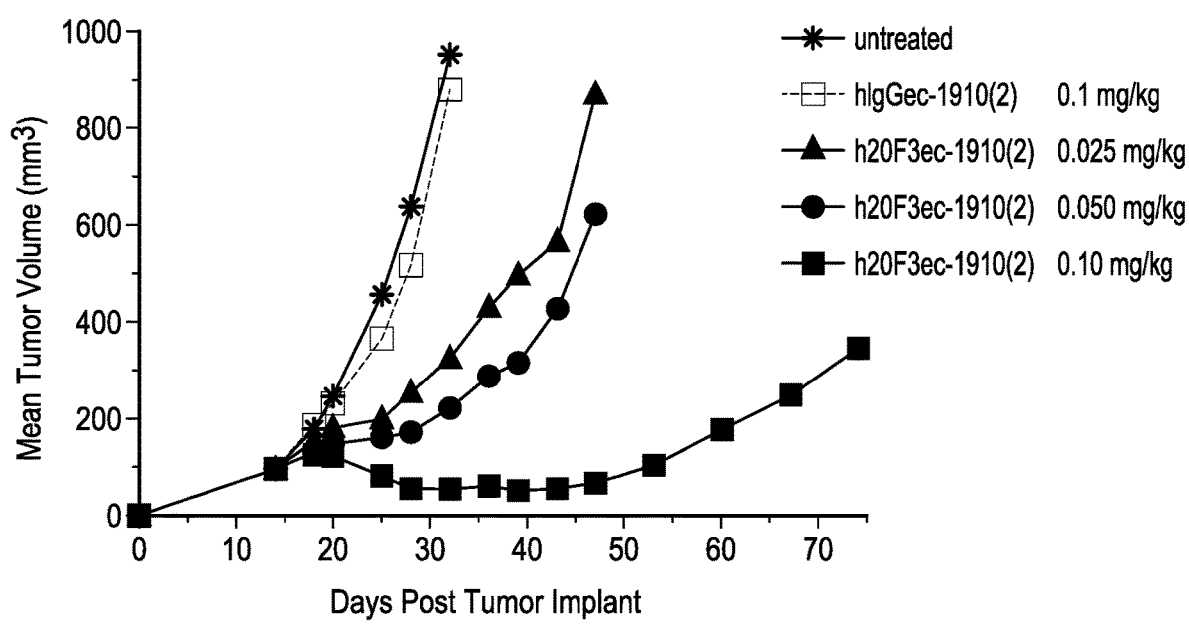
FIG. 12 shows the results of a non-Hodgkin lymphoma subcutaneous xenograft study in the WSU-DLCL2 cell line in SCID mice. The dose is indicated on the figure. The ADCs are both humanized 20F3 auristatin antibody drug conjugates.

SCID (C.B-17/Sz-Prkdc$^{scid}$) mice were implanted with 5 million WSU-DLCL2 non-Hodgkin lymphoma cells per animal subcutaneously. When mean tumor volume reached 100 mm$^3$, n=8 mice per treatment group were given a single intraperitoneal injection of h20F3ec-1910(2) PBD ADC or control hIgGec-1910(2) PBD ADC. PBD ADC dose levels examined were 100 ug/kg, 50 ug/kg, and 25 ug/kg. Individual mice were sacrificed when subcutaneous WSU-DLCL2 tumor volume reached 1,000 mm$^3$. As shown in FIG. 12, the HDLD h20F3ec-1910(2) PBD dimer ADCs produced durable complete responses 2/8 mice at the 100 ug/kg dose level. At the lower dose levels of 25 ug/kg and 50 ug/kg, h20F3ec-1910(2) PBD ADC produced measurable tumor growth delays relative to untreated mice. The hIgGec-1910(2) control PBD ADC had no antitumor activity at 100 ug/kg and produced 0/8 complete responses.

SEQUENCE LISTING

SEQ ID NO: 1 is the amino acid sequence of human NTB-A.
MLWLFQSLLFVFCFGPGNVVSQSSLTPLMVNGILGESVTLPLEFPAGEKVNFITWLFNETSLAFIVPHETK
SPEIHVTNPKQGKRLNFTQSYSLQLSNLKMEDTGSYRAQISTKTSAKLSSYTLRILRQLRNIQVTNHSQLFQ
NMTCELHLTCSVEDADDNVSFRWEALGNTLSSQPNLTVSWDPRISSEQDYTCIAENAVSNLSFSVSAQKL
CEDVKIQYTDTKMILFMVSGICIVFGFIILLLLVLRKRRDSLSLSTQRTQGPAESARNLEYVSVSPTNNTVYA
SVTHSNRETEIWTPRENDTITIYSTINHSKESKPTFSRATALDNVV SEQ ID NO: 2 is the amino acid sequence of cynonnolgus NTB-A.
MLWLFQSLLFVFCFGPGNLVSQSSSTPLMVNGVLGESVILPLELSAGEMIASITWLCNGTSLAFIEPSETKS
PNIRVTHPKQRKRLNFTQSYSLKLSNLEMEDTGSYSAQITTETSVKLSSYTLRIFRQLRSIQVNNYSQLFQN
RTCEIHLTCSVEDADDNVSFRWEALGSTLSSEPNITTSWDPRISGEQDYTCIAENAVSNLSFSVSAQKLCG
DVKIQYTDTKMILFVVFGICIVTGFIIMLLLVLRKRRDSLPLSTQRTQGPAEPAGNIEYVSVSPVNNTVYASV
THSNRETEISTPIKNATVTIYSTVNHSKESKPTFSRATALDNVV SEQ ID NO: 3 is the amino acid sequence of the mature heavy chain variable region of murine 20F3.
QIQLVQSGPELKKPGETVKISCKASGYTFTNYGMNWVKQAPGKDLKWMGWINTYSGEPRYADDFKGR
FAFSLEKSANTAYLQINNLKNEDMATYFCARDYGRWYFDVWGTGTTVTSS SEQ ID NO: 4 is the amino acid sequence of the mature heavy chain variable region of humanized 20F3 with no back mutations and with murine CDRs, as defined by Kabat.
QVQLVQSGSELKKPGASVKVSCKASGYTFTNYGMNWVRQAPGQGLEWMGWINTYSGEPRYADDFKG
RFVFSLDTSVSTAYLQISSLKAEDTAVYYCARDYGRWYFDVWGQGTTVTSS SEQ ID NO: 5 is the amino acid sequence of the mature heavy chain variable region of humanized 20F3 HA.
QVQLVQSGSELKKPGASVKVSCKASGYTFTNYGMNWVRQAPGQGLEWMGWINTYSGEPRYADDFKG
RFVFSLDTSVSTAYLQISSLKAEDTAVYYCARDYGRWYFDVWGQGTTVTSS SEQ ID NO: 6 is the amino acid sequence of the mature heavy chain variable region of humanized 20F3 HB.
QIQLVQSGSELKKPGASVKVSCKASGYTFTNYGMNWVRQAPGQGLEWMGWINTYSGEPRYADDFKG
RFVFSLDKSVSTAYLQISSLKAEDTAVYYCARDYGRWYFDVWGQGTTVTSS SEQ ID NO: 7 is the amino acid sequence of the mature heavy chain variable region of humanized 20F3 HC.
QIQLVQSGSELKKPGASVKVSCKASGYTFTNYGMNWVRQAPGQDLEWMGWINTYSGEPRYADDFKG
RFVFSLDKSVNTAYLQISSLKAEDTAVYYCARDYGRWYFDVWGQGTTVTSS SEQ ID NO: 8 is the amino acid sequence of the mature heavy chain variable region of humanized 20F3 HD.
QIQLVQSGSELKKPGASVKVSCKASGYTFTNYGMNWVRQAPGQDLKWMGWINTYSGEPRYADDFKG
RFVFSLDKSVNTAYLQISSLKAEDTAVYYCARDYGRWYFDVWGQGTTVTSS SEQ ID NO: 9 is the amino acid sequence of the mature heavy chain variable region of humanized 20F3 HE.
QIQLVQSGSELKKPGASVKVSCKASGYTFTNYGMNWVKQAPGQDLKWMGWINTYSGEPRYADDFKG
RFAFSLDKSVNTAYLQISSLKAEDTAVYFCARDYGRWYFDVWGQGTTVTSS SEQ ID NO: 10 is the amino acid sequence of CDR-H1 of murine and humanized 20F3, as defined by Kabat.
NYGMN SEQ ID NO: 11 is the amino acid sequence of CDR-H2 of murine and humanized 20F3, as defined by Kabat.
WINTYSGEPRYADDFKG SEQ ID NO: 12 is the amino acid sequence of CDR-H3 of murine and humanized 20F3, as defined by Kabat.
DYGRWYFDV SEQ ID NO: 13 is the amino acid sequence of the mature light chain variable region of murine 20F3.
QIVLSQSPAILSASPGEKVTMTCRASSSVSHMHWYQQKPGSSPKPWIYATSNLASGVPARFSGSGSGTSY
SLTISRVEAEDAATYYCQQWSSTPRTFGGGTKLEIKR SEQ ID NO: 14 is the amino acid sequence of the mature light chain variable region of humanized 20F3 with no back mutations and with murine CDRs, as defined by Kabat.
EIVLTQSPATLSLSPGERATLSCRASSSVSHMHWYQQKPGQAPRLLIYATSNLASGIPARFSGSGSGTDFTL
TISSLEPEDFAVYYCQQWSSTPRTFGGGTKVEIKR SEQ ID NO: 15 is the amino acid sequence of the mature light chain variable region of
humanized 20F3 LA.
EIVLTQSPATLSLSPGERATLSCRASSSVSHMHWYQQKPGQAPRLLIYATSNLASGIPARFSGSGSGTDFTL
TISSLEPEDFAVYYCQQWSSTPRTFGGGTKVEIKR SEQ ID NO: 16 is the amino acid sequence of the mature light chain variable region of humanized 20F3 LB.

EIVLTQSPATLSLSPGERATLSCRASSSVSHMHWYQQKPGQAPRPWIYATSNLASGIPARFSGSGSGTDY
TLTISSLEPEDFAVYYCQQWSSTPRTFGGGTKVEIKR

SEQ ID NO: 17 is the amino acid sequence of the mature light chain variable region of humanized 20F3 LC.
QIVLSQSPATLSLSPGERATLSCRASSSVSHMHWYQQKPGQAPRPWIYATSNLASGIPARFSGSGSGTDY
TLTISSLEPEDFAVYYCQQWSSTPRTFGGGTKVEIKR SEQ ID NO: 18 is the amino acid sequence of the mature light chain variable region of humanized 20F3 LD.
QIVLSQSPATLSLSPGERATMSCRASSSVSHMHWYQQKPGQAPRPWIYATSNLASGVPARFSGSGSGT
DYTLTISSLEPEDFAVYYCQQWSSTPRTFGGGTKVEIKR SEQ ID NO: 19 is the amino acid sequence of CDR-L1 of murine and humanized 20F3, as defined by Kabat.
RASSSVSHMH SEQ ID NO: 20 is the amino acid sequence of CDR-L2 of murine and humanized 20F3, as defined by Kabat.
ATSNLAS SEQ ID NO: 21 is the amino acid sequence of CDR-L3 of murine and humanized 20F3, as defined by Kabat.
QQWSSTPRT SEQ ID NO: 22 is the amino acid sequence of CDR-H1 of murine 20F3, as defined by IMGT.
GYTFTNYG SEQ ID NO: 23 is the amino acid sequence of CDR-H2 of murine 20F3, as defined by IMGT.
INTYSGEP SEQ ID NO: 24 is the amino acid sequence of CDR-H3 of murine 20F3, as defined by IMGT.
ARDYGRWYFDV SEQ ID NO: 25 is the amino acid sequence of CDR-L1 of murine 20F3, as defined by IMGT.
SSVSH The amino acid sequence of CDR-L2 of murine 20F3, as defined by IMGT is:
ATS SEQ ID NO: 26 is the amino acid sequence of CDR-L3 of murine 20F3, as defined by IMGT.
QQWSSTPRT SEQ ID NO: 27 is the amino acid sequence of a human light chain constant region.
TVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 28 is the amino acid sequence of a naturally occcuring human heavy chain constant region.
ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG SEQ ID NO: 29 is the amino acid sequence of a variant human heavy chain constant region (5239C).
ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGGPCVFLFPPKPKDTLMISRTPEVT
CVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG

What is claimed is:

1. An antibody that specifically binds to the human NTB-A protein wherein the antibody comprises a mature heavy chain variable region and a mature light chain variable region, wherein:
   (a) the mature heavy chain variable region comprises three heavy chain complementarity determining regions (CDRs) as defined by Kabat: heavy chain CDR1 consisting of SEQ ID NO:10, heavy chain CDR2 consisting of SEQ ID NO:11, and heavy chain CDR3 consisting of SEQ ID NO:12; and the mature light chain variable region comprises three light chain CDRs as defined by Kabat: light chain CDR1 consisting of SEQ ID NO:19, light chain CDR2 consisting of SEQ ID NO:20, and light chain CDR3 consisting of SEQ ID NO:21; or
   (b) the mature heavy chain variable region comprises three heavy chain complementarity determining regions (CDRs) as defined by IMGT: heavy chain CDR1 consisting of SEQ ID NO:22, heavy chain CDR2 consisting of SEQ ID NO:23, and heavy chain CDR3 consisting of SEQ ID NO:24; and the mature light chain variable region comprises three light chain CDRs as defined by IMGT: light chain CDR1 consisting of SEQ ID NO:25, light chain CDR2 consisting of the amino acid sequence ATS, and light chain CDR3 consisting of SEQ ID NO:26.

2. The antibody of claim 1 wherein the antibody is a humanized, chimeric or veneered antibody.

3. The antibody of claim 1, wherein the mature heavy chain region comprises an amino acid sequence as set forth in SEQ ID NO:8 and wherein the mature light chain variable region comprises an amino acid sequence as set forth in SEQ ID NO:18.

4. The antibody of claim 1 wherein the mature heavy chain and the mature light chain comprise amino acid sequences selected from the groups consisting of:
   SEQ ID NO:5 and SEQ ID NO:15, respectively;
   SEQ ID NO:5 and SEQ ID NO:16, respectively;
   SEQ ID NO:5 and SEQ ID NO:17, respectively;
   SEQ ID NO:5 and SEQ ID NO:18, respectively;
   SEQ ID NO:6 and SEQ ID NO:15, respectively;
   SEQ ID NO:6 and SEQ ID NO:16, respectively;
   SEQ ID NO:6 and SEQ ID NO:17, respectively;
   SEQ ID NO:6 and SEQ ID NO:18, respectively;
   SEQ ID NO:7 and SEQ ID NO:15, respectively;
   SEQ ID NO:7 and SEQ ID NO:16, respectively;
   SEQ ID NO:7 and SEQ ID NO:17, respectively;
   SEQ ID NO:7 and SEQ ID NO:18, respectively;
   SEQ ID NO:8 and SEQ ID NO:15, respectively;
   SEQ ID NO:8 and SEQ ID NO:16, respectively;
   SEQ ID NO:8 and SEQ ID NO:17, respectively;
   SEQ ID NO:8 and SEQ ID NO; 18, respectively;
   SEQ ID NO:9 and SEQ ID NO:15, respectively;
   SEQ ID NO:9 and SEQ ID NO:16, respectively;
   SEQ ID NO:9 and SEQ ID NO:17, respectively; and
   SEQ ID NO:9 and SEQ ID NO:18, respectively.

5. The antibody of claim 1 wherein the mature heavy chain variable region is fused to a heavy chain constant region and the mature light chain variable region is fused to a light chain constant region.

6. The antibody of claim 5, wherein the heavy chain constant region is a mutant form of natural human constant region, and wherein the heavy chain constant region has reduced binding to an Fcgamma receptor relative to the natural human constant region.

7. The antibody of claim 5, wherein the heavy chain constant region is of IgG1 isotype.

8. The antibody of claim 5, wherein the heavy chain constant region has an amino acid sequence comprising SEQ ID NO: 28 or SEQ ID NO: 29 and the light chain constant region has an amino acid sequence comprising SEQ ID NO: 27.

9. The antibody of claim 1, wherein the antibody is conjugated to a cytotoxic or cytostatic agent.

10. The antibody of claim 1, wherein the antibody is a humanized antibody.

11. The antibody of claim 10 wherein H2 is occupied by I or V, H38 is occupied by R or K, H44 is occupied by D or G, H46 is occupied by K or E, H68 is occupied by V or A, H73 is occupied by K or T, H76 is occupied by N or S, H91 is occupied by Y or F, L1 is occupied by Q or E, L5 is occupied by S or T, L21 is occupied by M or L, L46 is occupied by P or L, L47 is occupied by W or L, L58 is occupied by V or I, and L71 is occupied by Y or F; numbering is via the Kabat numbering system.

12. The antibody of claim 10 wherein the following variable region frameworks positions are occupied as specified: H2 occupied by I, H38 occupied by R, H44 occupied by D, H46 occupied by K, H68 occupied by V, H73 occupied by K, H76 occupied by N, H91 occupied by Y, L1 occupied by Q, L5 occupied by S, L21 occupied by M, L46 occupied by P, L47 occupied by W, L58 occupied by V, L71 occupied by Y; numbering is via the Kabat numbering system.

13. The antibody of claim 10 wherein the following variable region frameworks positions are occupied as specified: H2 occupied by I, H44 occupied by D, H46 occupied by K, H73 occupied by K, H76 occupied by N, L1 occupied by Q, L5 occupied by S, L21 occupied by M, L46 occupied by P, L47 occupied by W, L58 occupied by V, L71 occupied by Y; numbering is via the Kabat numbering system.

14. The antibody of claim 1, wherein the antibody is conjugated to a cytotoxic agent.

15. The antibody of claim 14 wherein the cytotoxic agent is a maytansinoid, auristatin, pyrrolo[1,4]benzodiazepine, indolinobenzodiazepine, or oxazolidinobenzodiazepine.

16. The antibody of claim 15 wherein the cytotoxic agent is

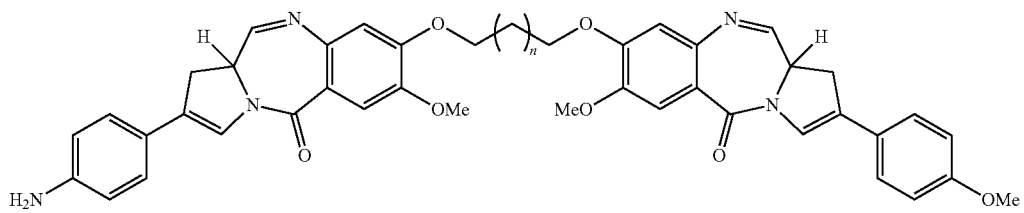

wherein the subscript n is 1 or 3.

17. The antibody of claim 1, wherein the antibody comprises a scFv.

18. The antibody of claim 17, wherein the antibody consists of a scFv.

19. The antibody of claim 1, wherein the antibody is a bispecific antibody.

20. An anti-NTB-A antibody-drug conjugate compound having the formula

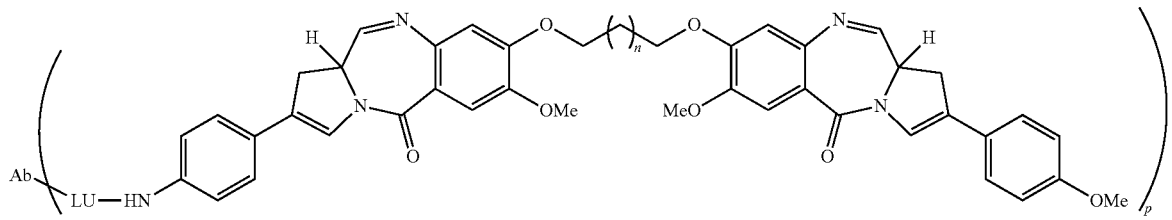

wherein:
the subscript n is 1 or 3;
LU is a cleavable Linker Unit;
Ab is an antibody as set forth in claim 1; and
the subscript p is an integer from 1 to 4.

21. An anti-NTB-A antibody-drug conjugate compound of claim 20 having the formula

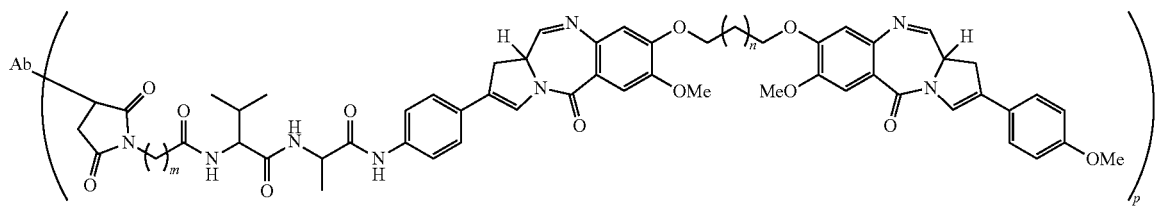

wherein:
the subscript n is 1 or 3;
the subscript m is 2 to 5
Ab is an antibody as set forth in claim 1; and
the subscript p is an integer from 1 to 4.

22. The antibody-drug conjugate compound of claim 21 having the formula:

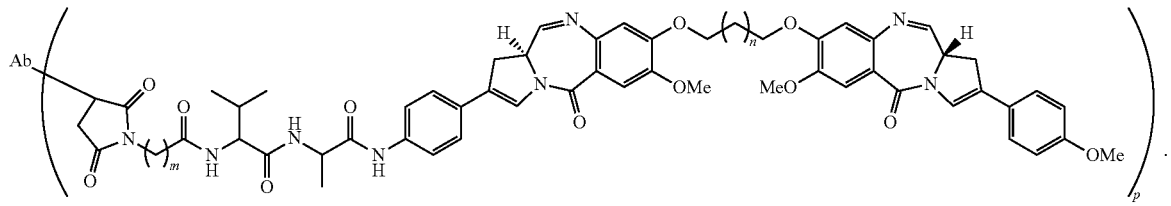

23. The antibody-drug conjugate compound of claim 21 having the formula:

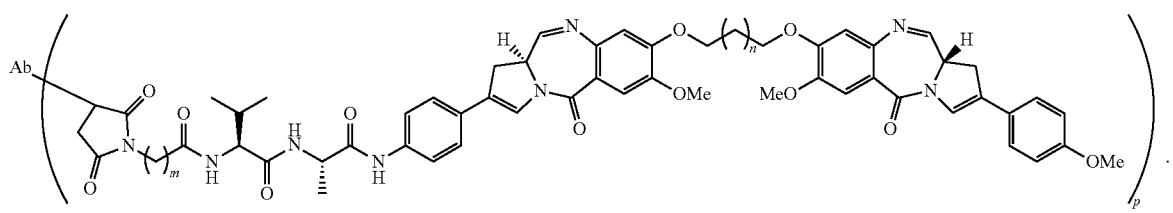

24. The antibody-drug conjugate compound of claim 21 wherein attachment to Ab is via a sulfur atom of an engineered cysteine residue of Ab.

25. The antibody-drug conjugate compound of claim 21 wherein attachment to Ab is via a sulfur atom or an engineered cysteine residue at position 239 of the heavy chain constant region, according to the EU index system of numbering.

26. The antibody-drug conjugate compound of claim 20 wherein p is 2.

27. An antibody-drug conjugate composition comprising a population of anti-NTB-A antibody-drug conjugate molecules having the formula:

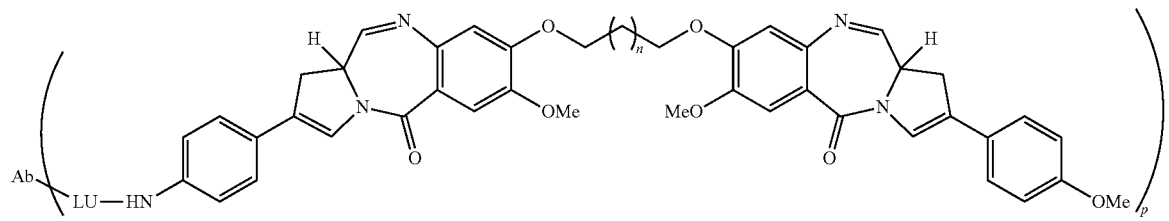

wherein:
the subscript n is 1 to 3;
LU is a cleavable Linker Unit;
Ab is an antibody as set forth in claim 1; and
the subscript p is an integer from 1 to 4;
wherein the average drug load of the composition is about 2.

28. An antibody-drug conjugate composition of claim 27 comprising a population of anti-NTB-A antibody-drug conjugate molecules having the formula:

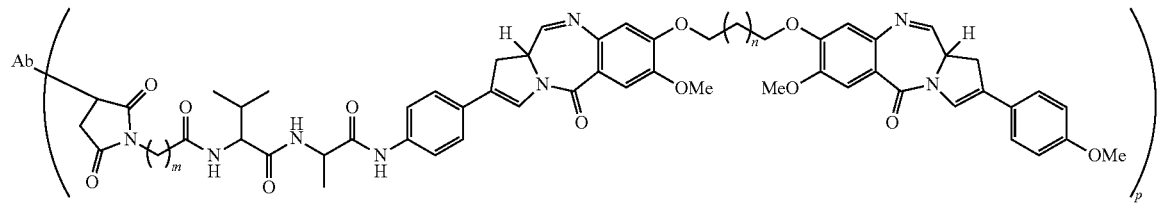

wherein
the subscript n is 1 to 3;
the subscript m is 2 to 5
Ab is an antibody as set forth in claim 1; and
the subscript p is an integer from 1 to 4;
wherein the average drug load of the composition is about 2.

29. The composition of claim 28 wherein the antibody-drug conjugate molecules have the formula:

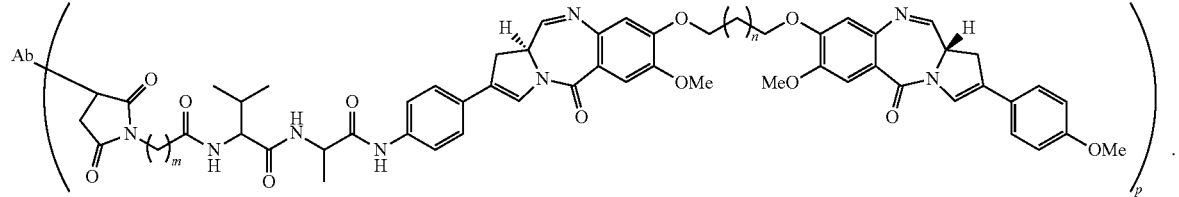

30. The composition of claim 28 wherein the antibody-drug conjugate molecules have the formula:

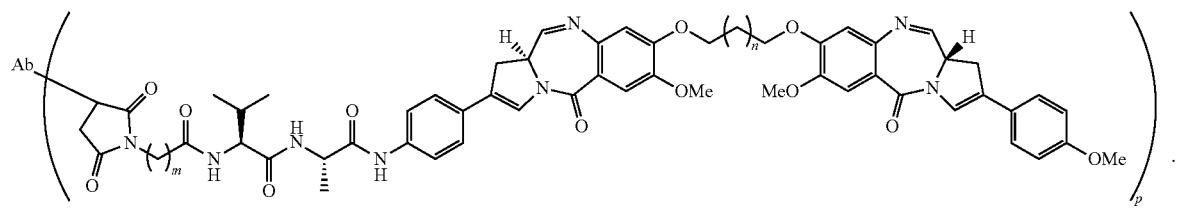

31. The composition of claim 28 wherein attachment to Ab is via a sulfur atom of an engineered cysteine residue of Ab.

32. The composition of claim 28 wherein attachment to Ab is via a sulfur atom or an engineered cysteine residue at position 239 of the heavy chain constant region, according to the EU index system of numbering.

33. A pharmaceutical composition comprising a population of anti-NTB-A antibody-drug conjugate molecules and a pharmaceutically acceptable carrier, wherein the anti-NTB-A antibody-drug conjugate molecules have the formula:

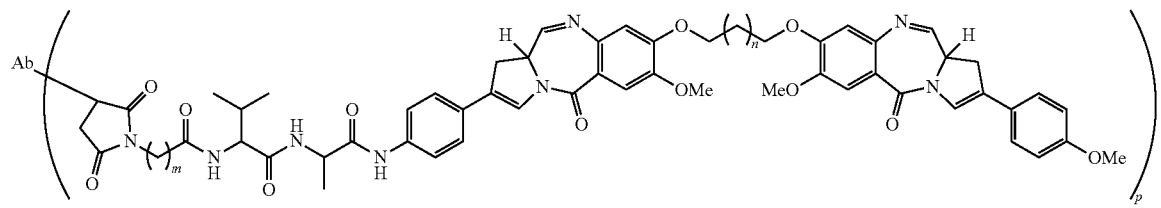

wherein:
the subscript n is 1 to 3;
the subscript m is 2 to 5
Ab is an antibody as set forth in claim 1; and
the subscript p is an integer from 1 to 4;
wherein the average drug load of the composition is about 2.

34. The pharmaceutical composition of claim 33 wherein the antibody-drug conjugate molecules have the formula:

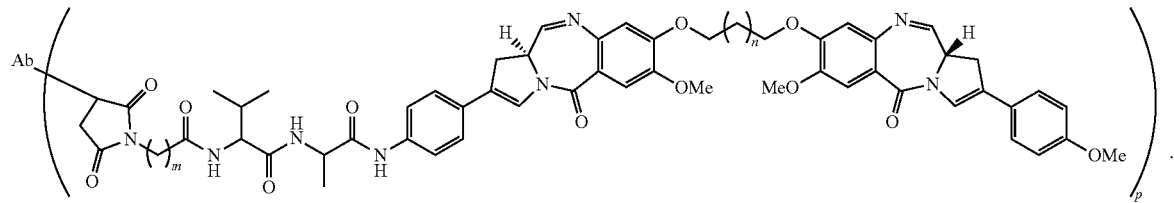

35. The pharmaceutical composition of claim 33 wherein the antibody-drug conjugate molecules have the formula:

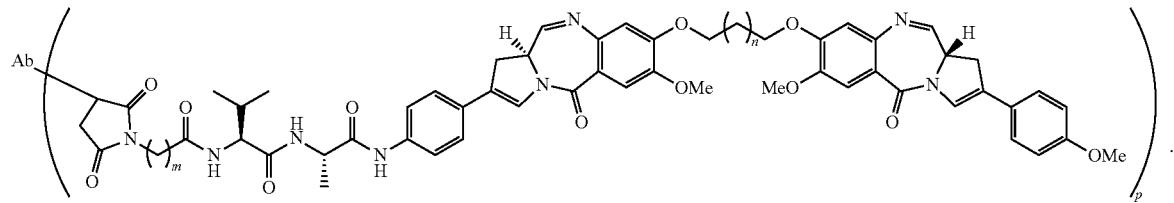

36. The pharmaceutical composition of claim 33 wherein attachment to Ab is via a sulfur atom of an engineered cysteine residue of Ab.

37. The pharmaceutical composition of claim 33 wherein attachment to Ab is via a sulfur atom or an engineered cysteine residue at position 239 of the heavy chain constant region, according to the EU index system of numbering.

38. A method of treating a patient having a cancer that expresses NTB-A, comprising administering to the patient an effective regimen of a composition of claim 27.

39. The method of claim 38, wherein the cancer is multiple myeloma, non-Hodgkin lymphoma, acute myeloid leukemia, chronic lymphocytic leukemia, Waldenström's macroglobulinemia, or monoclonal gammopathy of undetermined significance (MGUS).

40. The method of claim 38, wherein the cancer is a T-cell lymphoma.

41. A method of treating a patient having an autoimmune disease, comprising administering to the patient an effective regimen of a composition of claim 27.

42. A pharmaceutical composition comprising an antibody of claim 1; and a pharmaceutically acceptable carrier.

43. An antibody that specifically binds to the human NTB-A protein wherein the antibody comprises the three heavy chain CDRs as set forth in SEQ ID NOs: 10-12 and the three light chain CDRs as set forth in SEQ ID NOs: 19-21.

44. The antibody of claim 43, wherein the antibody comprises a scFv.

45. The antibody of claim 44, wherein the antibody consists of a scFv.

46. The antibody of claim 43, wherein the antibody is a bispecific antibody.

47. A nucleic acid comprising a sequence encoding a heavy chain variable region comprising the three heavy chain CDRs of SEQ ID NO: 3 and/or a light chain variable region comprising the three light chain CDRs of SEQ ID NO: 13, wherein the CDRs are defined by Kabat or IMGT, and wherein the heavy chain variable region and the light chain variable region together bind to human NTB-A.

48. The nucleic acid of claim 47, comprising a sequence encoding a mature heavy chain region having the amino acid sequence set forth in SEQ ID NO: 8 and/or a light chain variable region having the amino acid sequence set forth in SEQ ID NO: 18.

49. A vector comprising the nucleic acid of claim 47.

50. A host cell comprising the vector of claim 49.

51. The host cell of claim 50, wherein the host cell is a CHO cell.

52. A method of making an anti-NTB-A antibody or antigen binding fragment thereof, wherein the method comprises culturing the host cell of claim 50 under conditions suitable for expression of the nucleic acid encoding the antibody or antigen binding fragment thereof.

53. The method of claim 52, wherein the host cell is a CHO cell.

54. A method of making an anti-NTB-A antibody drug conjugate, wherein the method comprises:
   a) culturing the host cell of claim 50 under conditions suitable for expression of the nucleic acid encoding the antibody or antigen binding fragment thereof;
   b) isolating the antibody or antigen binding fragment thereof; and
   c) conjugating a cytotoxic agent to the antibody or antigen binding fragment thereof.

55. The method of claim 54, wherein the host cell is a CHO cell.

56. The method of claim 54, wherein the cytotoxic agent is a maytansinoid, auristatin, pyrrolo[1,4]benzodiazepine, indolinobenzodiazepine, or oxazolidinobenzodiazepine.

57. A method of treating a patient having a hematological cancer that expresses NTB-A, comprising administering to the patient an effective regimen of a composition comprising a population of anti-NTB-A antibody-drug conjugate molecules having the formula:

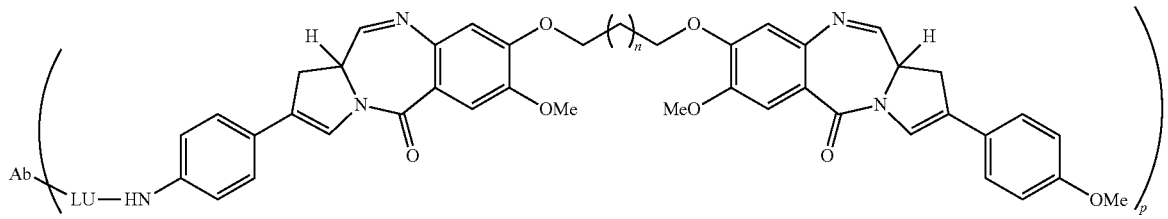

wherein:
the subscript n is 1 to 3;
LU is a cleavable Linker Unit;
Ab is an antibody comprising the three heavy chain CDRs of SEQ ID NO: 3 and the three light chain CDRs of SEQ ID NO: 13 wherein the CDRs are as defined by Kabat or IMGT; and
the subscript p is an integer from 1 to 4;
wherein the average drug load of the composition is about 2.

58. The method of claim 57, wherein the cancer is a multiple myeloma, non-Hodgkin lymphoma, acute myeloid leukemia, chronic lymphocytic leukemia, Waldenström's macroglobulinemia, or monoclonal gammopathy of undetermined significance (MGUS).

59. The method of claim 57, wherein the cancer is a T-cell lymphoma.

60. A pharmaceutical composition comprising a population of anti-NTB-A antibody-drug conjugate molecules having the formula:

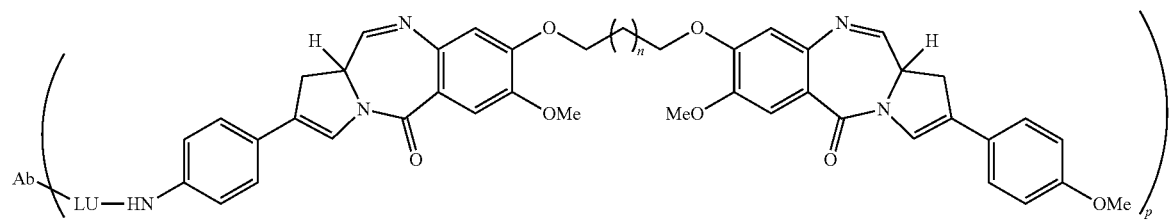

wherein:
the subscript n is 1 to 3;
LU is a cleavable Linker Unit;
Ab is an antibody comprising a mature heavy chain region having a heavy chain variable region having the amino acid sequence set forth in SEQ ID NO: 8 and a heavy chain constant region having the amino acid sequence set forth in SEQ ID NO: 29, and a light chain region having a light chain variable region having the amino acid sequence set forth in SEQ ID NO: 18 and a light chain constant region having the amino acid sequence set forth in SEQ ID NO: 27; and
the subscript p is an integer from 1 to 4;
wherein the average drug load of the composition is about 2.

61. A method of treating a patient having a hematological cancer that expresses NTB-A, comprising administering to the patient an effective amount of the anti-NTB-A antibody-drug conjugate compound of claim 20.

62. The method of claim 61, wherein the cancer is multiple myeloma, non-Hodgkin lymphoma, acute myeloid leukemia, chronic lymphocytic leukemia, Waldenström's macroglobulinemia, or monoclonal gammopathy of undetermined significance (MGUS).

63. The method of claim 61, wherein the cancer is T-cell lymphoma.

64. A method of treating a patient having an autoimmune disease, comprising administering to the patient an effective amount of the anti-NTB-A antibody-drug conjugate compound of claim 20.

65. An antibody-drug conjugate comprising an antibody and a drug wherein the antibody is conjugated to the drug, wherein the antibody specifically binds to human NTB-A protein, the antibody comprising a mature heavy chain variable region and a mature light chain variable region, wherein:

(a) the mature heavy chain variable region comprises three heavy chain complementarity determining regions (CDRs) as defined by Kabat: heavy chain CDR1 consisting of SEQ ID NO:10, heavy chain CDR2 consisting of SEQ ID NO:11, and heavy chain CDR3 consisting of SEQ ID NO:12; and the mature light chain variable region comprises three light chain CDRs as defined by Kabat: light chain CDR1 consisting of SEQ ID NO:19, light chain CDR2 consisting of SEQ ID NO:20, and light chain CDR3 consisting of SEQ ID NO:21; or (b) the mature heavy chain variable region comprises three heavy chain complementarity determining regions (CDRs) as defined by IMGT: heavy chain CDR1 consisting of SEQ ID NO:22, heavy chain CDR2 consisting of SEQ ID NO:23, and heavy chain CDR3 consisting of SEQ ID NO:24; and the mature light chain variable region comprises three light chain CDRs as defined by IMGT: light chain CDR1 consisting of SEQ ID NO:25, light chain CDR2 consisting of the amino acid sequence ATS, and light chain CDR3 consisting of SEQ ID NO:26,
wherein the drug is a cytostatic agent or a cytotoxic agent.

66. The antibody-drug conjugate of claim 65 wherein the drug is a cytotoxic agent.

67. The antibody-drug conjugate of claim 66 wherein the cytotoxic agent is a maytansinoid, auristatin, pyrrolo[1,4]benzodiazepine, indolinobenzodiazepine, or oxazolidinobenzodiazepine.

68. The antibody-drug conjugate of claim 67 wherein the cytotoxic agent is an auristatin.

69. The antibody-drug conjugate of claim 68 wherein the cytotoxic agent is MMAE.

70. The antibody-drug conjugate of claim 68 wherein the cytotoxic agent is MMAF.

71. The antibody-drug conjugate of claim 68 wherein the cytotoxic agent is Auristatin-2.

72. The antibody-drug conjugate of claim 69, wherein the antibody comprises a scFv.

73. The antibody-drug conjugate of claim 72, wherein the antibody consists of a scFv.

74. The antibody-drug conjugate of claim 69, wherein the antibody is a bispecific antibody.

75. The antibody-drug conjugate of claim 66 wherein the cytotoxic agent is a camptothecin.

76. The antibody-drug conjugate of claim 65, wherein the antibody comprises a scFv.

77. The antibody-drug conjugate of claim 76, wherein the antibody consists of a scFv.

78. The antibody-drug conjugate of claim 65, where the antibody is a bispecific antibody.

79. A method of treating a patient having a hematological cancer that expresses NTB-A, comprising administering to the patient an effective regime of the antibody-drug conjugate of claim 65.

80. The method of claim 79, wherein the cancer is multiple myeloma, non-Hodgkin lymphoma, acute myeloid leukemia, chronic lymphocytic leukemia, Waldenström's macroglobulinemia, or monoclonal gammopathy of undetermined significance (MGUS).

81. The method of claim 79, wherein the cancer is a T-cell lymphoma.

82. A method of treating a patient having an autoimmune disease, comprising administering to the patient an effective regimen of the antibody-drug conjugate of claim 65.

83. A method of treating a patient having a hematological cancer that expresses NTB-A, comprising administering to the patient an effective regime of the antibody-drug conjugate of claim 75.

84. The method of claim 83, wherein the cancer is multiple myeloma, non-Hodgkin lymphoma, acute myeloid leukemia, chronic lymphocytic leukemia, Waldenström's macroglobulinemia, or monoclonal gammopathy of undetermined significance (MGUS).

85. The method of claim 83, wherein the cancer is a T-cell lymphoma.

86. A method of treating a patient having an autoimmune disease, comprising administering to the patient an effective regimen of the antibody-drug conjugate of claim 75.

87. A method of treating a patient having a hematological cancer that expresses NTB-A, comprising administering to the patient an effective regime of the antibody-drug conjugate of claim 68.

88. The method of claim 87, wherein the cancer is multiple myeloma, non-Hodgkin lymphoma, acute myeloid leukemia, chronic lymphocytic leukemia, Waldenström's macroglobulinemia, or monoclonal gammopathy of undetermined significance (MGUS).

89. The method of claim 87, wherein the cancer is a T-cell lymphoma.

90. A method of treating a patient having an autoimmune disease, comprising administering to the patient an effective regimen of the antibody-drug conjugate of claim 68.

\* \* \* \* \*

SEQUENCE LISTING

<160> NUMBER OF SEQ ID NOS: 29

<210> SEQ ID NO 1
<211> LENGTH: 332

```
<212> TYPE: PRT
<213> ORGANISM: Homo sapiens

<400> SEQUENCE: 1

Met Leu Trp Leu Phe Gln Ser Leu Leu Phe Val Phe Cys Phe Gly Pro
1               5                   10                  15

Gly Asn Val Val Ser Gln Ser Ser Leu Thr Pro Leu Met Val Asn Gly
            20                  25                  30

Ile Leu Gly Glu Ser Val Thr Leu Pro Leu Glu Phe Pro Ala Gly Glu
        35                  40                  45

Lys Val Asn Phe Ile Thr Trp Leu Phe Asn Glu Thr Ser Leu Ala Phe
    50                  55                  60

Ile Val Pro His Glu Thr Lys Ser Pro Glu Ile His Val Thr Asn Pro
65                  70                  75                  80

Lys Gln Gly Lys Arg Leu Asn Phe Thr Gln Ser Tyr Ser Leu Gln Leu
                85                  90                  95

Ser Asn Leu Lys Met Glu Asp Thr Gly Ser Tyr Arg Ala Gln Ile Ser
            100                 105                 110

Thr Lys Thr Ser Ala Lys Leu Ser Ser Tyr Thr Leu Arg Ile Leu Arg
        115                 120                 125

Gln Leu Arg Asn Ile Gln Val Thr Asn His Ser Gln Leu Phe Gln Asn
    130                 135                 140

Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
            180                 185                 190

Tyr Thr Cys Ile Ala Glu Asn Ala Val Ser Asn Leu Ser Phe Ser Val
        195                 200                 205

Ser Ala Gln Lys Leu Cys Glu Asp Val Lys Ile Gln Tyr Thr Asp Thr
    210                 215                 220

Lys Met Ile Leu Phe Met Val Ser Gly Ile Cys Ile Val Phe Gly Phe
225                 230                 235                 240

Ile Ile Leu Leu Leu Leu Val Leu Arg Lys Arg Arg Asp Ser Leu Ser
                245                 250                 255

Leu Ser Thr Gln Arg Thr Gln Gly Pro Ala Glu Ser Ala Arg Asn Leu
            260                 265                 270

Glu Tyr Val Ser Val Ser Pro Thr Asn Asn Thr Val Tyr Ala Ser Val
        275                 280                 285

Thr His Ser Asn Arg Glu Thr Glu Ile Trp Thr Pro Arg Glu Asn Asp
    290                 295                 300

Thr Ile Thr Ile Tyr Ser Thr Ile Asn His Ser Lys Glu Ser Lys Pro
305                 310                 315                 320

Thr Phe Ser Arg Ala Thr Ala Leu Asp Asn Val Val
                325                 330

<210> SEQ ID NO 2
<211> LENGTH: 332
<212> TYPE: PRT
<213> ORGANISM: Macaca fascicularis

<400> SEQUENCE: 2

Met Leu Trp Leu Phe Gln Ser Leu Leu Phe Val Phe Cys Phe Gly Pro
1               5                   10                  15
```

Gly Asn Leu Val Ser Gln Ser Ser Thr Pro Leu Met Val Asn Gly
            20                  25                  30

Val Leu Gly Glu Ser Val Ile Leu Pro Leu Glu Leu Ser Ala Gly Glu
        35                  40                  45

Met Ile Ala Ser Ile Thr Trp Leu Cys Asn Gly Thr Ser Leu Ala Phe
 50                  55                  60

Ile Glu Pro Ser Glu Thr Lys Ser Pro Asn Ile Arg Val Thr His Pro
 65                  70                  75                  80

Lys Gln Arg Lys Arg Leu Asn Phe Thr Gln Ser Tyr Ser Leu Lys Leu
                85                  90                  95

Ser Asn Leu Glu Met Glu Asp Thr Gly Ser Tyr Ser Ala Gln Ile Thr
            100                 105                 110

Thr Glu Thr Ser Val Lys Leu Ser Ser Tyr Thr Leu Arg Ile Phe Arg
        115                 120                 125

Gln Leu Arg Ser Ile Gln Val Asn Asn Tyr Ser Gln Leu Phe Gln Asn
    130                 135                 140

Arg Thr Cys Glu Ile His Leu Thr Cys Ser Val Glu Asp Ala Asp Asp
145                 150                 155                 160

Asn Val Ser Phe Arg Trp Glu Ala Leu Gly Ser Thr Leu Ser Ser Glu
                165                 170                 175

Pro Asn Ile Thr Thr Ser Trp Asp Pro Arg Ile Ser Gly Glu Gln Asp
            180                 185                 190

Tyr Thr Cys Ile Ala Glu Asn Ala Val Ser Asn Leu Ser Phe Ser Val
        195                 200                 205

Ser Ala Gln Lys Leu Cys Gly Asp Val Lys Ile Gln Tyr Thr Asp Thr
    210                 215                 220

Lys Met Ile Leu Phe Val Val Phe Gly Ile Cys Ile Val Thr Gly Phe
225                 230                 235                 240

Ile Ile Met Leu Leu Leu Val Leu Arg Lys Arg Arg Asp Ser Leu Pro
                245                 250                 255

Leu Ser Thr Gln Arg Thr Gln Gly Pro Ala Glu Pro Ala Gly Asn Ile
            260                 265                 270

Glu Tyr Val Ser Val Ser Pro Val Asn Asn Thr Val Tyr Ala Ser Val
        275                 280                 285

Thr His Ser Asn Arg Glu Thr Glu Ile Ser Thr Pro Ile Lys Asn Ala
    290                 295                 300

Thr Val Thr Ile Tyr Ser Thr Val Asn His Ser Lys Glu Ser Lys Pro
305                 310                 315                 320

Thr Phe Ser Arg Ala Thr Ala Leu Asp Asn Val Val
                325                 330

<210> SEQ ID NO 3
<211> LENGTH: 118
<212> TYPE: PRT
<213> ORGANISM: Mus musculus

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Asp Leu Lys Trp Met
        35                  40                  45

Gly Trp Ile Asn Thr Tyr Ser Gly Glu Pro Arg Tyr Ala Asp Asp Phe
 50                  55                  60

Lys Gly Arg Phe Ala Phe Ser Leu Glu Lys Ser Ala Asn Thr Ala Tyr
65                  70                  75                  80

Leu Gln Ile Asn Asn Leu Lys Asn Glu Asp Met Ala Thr Tyr Phe Cys
                85                  90                  95

Ala Arg Asp Tyr Gly Arg Trp Tyr Phe Asp Val Trp Gly Thr Gly Thr
            100                 105                 110

Thr Val Thr Val Ser Ser
        115

<210> SEQ ID NO 4
<211> LENGTH: 118
<212> TYPE: PRT
<213> ORGANISM: Artificial
<220> FEATURE:
<223> OTHER INFORMATION: mature heavy chain variable region of humanized
      20F3 with no back mutations

<400> SEQUENCE: 4

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ser Gly Glu Pro Arg Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
            100                 105                 110

Thr Val Thr Val Ser Ser
        115

<210> SEQ ID NO 5
<211> LENGTH: 118
<212> TYPE: PRT
<213> ORGANISM: Artificial
<220> FEATURE:
<223> OTHER INFORMATION: mature heavy chain variable region of humanized
      20F3 HA

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ser Gly Glu Pro Arg Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
            100                 105                 110

Thr Val Thr Val Ser Ser
        115

<210> SEQ ID NO 6
<211> LENGTH: 118
<212> TYPE: PRT
<213> ORGANISM: Artificial
<220> FEATURE:
<223> OTHER INFORMATION: mature heavy chain variable region of humanized
      20F3 HB

<400> SEQUENCE: 6

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Ser Gly Glu Pro Arg Tyr Ala Asp Asp Phe
    50                  55                  60

Lys Gly Arg Phe Val Phe Ser Leu Asp Lys Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
            100                 105                 110

Thr Val Thr Val Ser Ser
        115

<210> SEQ ID NO 7
<211> LENGTH: 118
<212> TYPE: PRT
<213> ORGANISM: Artificial
<220> FEATURE:
<223> OTHER INFORMATION: mature heavy chain variable region of humanized
      20F3 HC

<400> SEQUENCE: 7

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Asp Leu Glu Trp Met
        35                  40                  45

Gly Trp Ile Asn Thr Tyr Ser Gly Glu Pro Arg Tyr Ala Asp Asp Phe
    50                  55                  60

Lys Gly Arg Phe Val Phe Ser Leu Asp Lys Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
            100                 105                 110

Thr Val Thr Val Ser Ser
        115

<210> SEQ ID NO 8
<211> LENGTH: 118
<212> TYPE: PRT
<213> ORGANISM: Artificial

```
<220> FEATURE:
<223> OTHER INFORMATION: mature heavy chain variable region of humanized
      20F3 HD

<400> SEQUENCE: 8

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Asp Leu Lys Trp Met
            35                  40                  45

Gly Trp Ile Asn Thr Tyr Ser Gly Glu Pro Arg Tyr Ala Asp Asp Phe
        50                  55                  60

Lys Gly Arg Phe Val Phe Ser Leu Asp Lys Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
                100                 105                 110

Thr Val Thr Val Ser Ser
            115

<210> SEQ ID NO 9
<211> LENGTH: 118
<212> TYPE: PRT
<213> ORGANISM: Artificial
<220> FEATURE:
<223> OTHER INFORMATION: mature heavy chain variable region of humanized
      20F3 HE

<400> SEQUENCE: 9

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Asp Leu Lys Trp Met
            35                  40                  45

Gly Trp Ile Asn Thr Tyr Ser Gly Glu Pro Arg Tyr Ala Asp Asp Phe
        50                  55                  60

Lys Gly Arg Phe Ala Phe Ser Leu Asp Lys Ser Val Asn Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Gly Arg Trp Tyr Phe Asp Val Trp Gly Gln Gly Thr
                100                 105                 110

Thr Val Thr Val Ser Ser
            115

<210> SEQ ID NO 10
<211> LENGTH: 5
<212> TYPE: PRT
<213> ORGANISM: Mus musculus

<400> SEQUENCE: 10

Asn Tyr Gly Met Asn
1               5

<210> SEQ ID NO 11
<211> LENGTH: 17
```

```
<212> TYPE: PRT
<213> ORGANISM: Mus musculus

<400> SEQUENCE: 11

Trp Ile Asn Thr Tyr Ser Gly Glu Pro Arg Tyr Ala Asp Asp Phe Lys
1               5                   10                  15

Gly

<210> SEQ ID NO 12
<211> LENGTH: 9
<212> TYPE: PRT
<213> ORGANISM: Mus musculus

<400> SEQUENCE: 12

Asp Tyr Gly Arg Trp Tyr Phe Asp Val
1               5

<210> SEQ ID NO 13
<211> LENGTH: 107
<212> TYPE: PRT
<213> ORGANISM: Mus musculus

<400> SEQUENCE: 13

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser His Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Thr Pro Arg Thr
                85                  90                  95

Phe Gly Gly Gly Thr Lys Leu Glu Ile Lys Arg
            100                 105

<210> SEQ ID NO 14
<211> LENGTH: 107
<212> TYPE: PRT
<213> ORGANISM: Artificial
<220> FEATURE:
<223> OTHER INFORMATION: mature light chain variable region of humanized
      20F3 with no back mutations

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser His Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
                85                  90                  95
```

```
Phe Gly Gly Gly Thr Lys Val Glu Ile Lys Arg
            100                 105

<210> SEQ ID NO 15
<211> LENGTH: 107
<212> TYPE: PRT
<213> ORGANISM: Artificial
<220> FEATURE:
<223> OTHER INFORMATION: mature light chain variable region of humanized
      20F3 LA

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser His Met
            20                  25                  30

His Trp Tyr Gln Gln Lys Pro Gly Gln Ala Pro Arg Leu Leu Ile Tyr
            35                  40                  45

Ala Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
                85                  90                  95

Phe Gly Gly Gly Thr Lys Val Glu Ile Lys Arg
            100                 105

<210> SEQ ID NO 16
<211> LENGTH: 107
<212> TYPE: PRT
<213> ORGANISM: Artificial
<220> FEATURE:
<223> OTHER INFORMATION: mature light chain variable region of humanized
      20F3 LB

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser His Met
            20                  25                  30

His Trp Tyr Gln Gln Lys Pro Gly Gln Ala Pro Arg Pro Trp Ile Tyr
            35                  40                  45

Ala Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
                85                  90                  95

Phe Gly Gly Gly Thr Lys Val Glu Ile Lys Arg
            100                 105

<210> SEQ ID NO 17
<211> LENGTH: 107
<212> TYPE: PRT
<213> ORGANISM: Artificial
<220> FEATURE:
<223> OTHER INFORMATION: mature light chain variable region of humanized
      20F3 LC

<400> SEQUENCE: 17

Gln Ile Val Leu Ser Gln Ser Pro Ala Thr Leu Ser Leu Ser Pro Gly
```

```
            1               5                  10                 15
        Glu Arg Ala Thr Leu Ser Cys Arg Ala Ser Ser Ser Val Ser His Met
                       20                  25                 30

His Trp Tyr Gln Gln Lys Pro Gly Gln Ala Pro Arg Pro Trp Ile Tyr
                       35                  40                 45

Ala Thr Ser Asn Leu Ala Ser Gly Ile Pro Ala Arg Phe Ser Gly Ser
                50                  55                  60

Gly Ser Gly Thr Asp Tyr Thr Leu Thr Ile Ser Ser Leu Glu Pro Glu
        65                  70                  75                  80

Asp Phe Ala Val Tyr Tyr Cys Gln Gln Trp Ser Ser Thr Pro Arg Thr
                        85                  90                  95

Phe Gly Gly Gly Thr Lys Val Glu Ile Lys Arg
                       100                 105
```

<210> SEQ ID NO 18
<211> LENGTH: 107
<212> TYPE: PRT
<213> ORGANISM: Artificial
<220> FEATURE:
<223> OTHER INFORMATION: mature light chain variable region of humanized 20F3 LD

<400> SEQUENCE: 18

```
        Gln Ile Val Leu Ser Gln Ser Pro Ala Thr Leu Ser Leu Ser Pro Gly
        1               5                  10                 15

Glu Arg Ala Thr Met Ser Cys Arg Ala Ser Ser Ser Val Ser His Met
                       20                  25                 30

His Trp Tyr Gln Gln Lys Pro Gly Gln Ala Pro Arg Pro Trp Ile Tyr
                       35                  40                 45

Ala Thr Ser Asn Leu Ala Ser Gly Val Pro Ala Arg Phe Ser Gly Ser
                50                  55                  60

Gly Ser Gly Thr Asp Tyr Thr Leu Thr Ile Ser Ser Leu Glu Pro Glu
        65                  70                  75                  80

Asp Phe Ala Val Tyr Tyr Cys Gln Gln Trp Ser Ser Thr Pro Arg Thr
                        85                  90                  95

Phe Gly Gly Gly Thr Lys Val Glu Ile Lys Arg
                       100                 105
```

<210> SEQ ID NO 19
<211> LENGTH: 10
<212> TYPE: PRT
<213> ORGANISM: Mus musculus

<400> SEQUENCE: 19

```
        Arg Ala Ser Ser Ser Val Ser His Met His
        1               5                  10
```

<210> SEQ ID NO 20
<211> LENGTH: 7
<212> TYPE: PRT
<213> ORGANISM: Mus musculus

<400> SEQUENCE: 20

```
        Ala Thr Ser Asn Leu Ala Ser
        1               5
```

<210> SEQ ID NO 21
<211> LENGTH: 9
<212> TYPE: PRT
<213> ORGANISM: Mus musculus

```
<400> SEQUENCE: 21

Gln Gln Trp Ser Ser Thr Pro Arg Thr
1               5

<210> SEQ ID NO 22
<211> LENGTH: 8
<212> TYPE: PRT
<213> ORGANISM: Mus musculus

<400> SEQUENCE: 22

Gly Tyr Thr Phe Thr Asn Tyr Gly
1               5

<210> SEQ ID NO 23
<211> LENGTH: 8
<212> TYPE: PRT
<213> ORGANISM: Mus musculus

<400> SEQUENCE: 23

Ile Asn Thr Tyr Ser Gly Glu Pro
1               5

<210> SEQ ID NO 24
<211> LENGTH: 11
<212> TYPE: PRT
<213> ORGANISM: Mus musculus

<400> SEQUENCE: 24

Ala Arg Asp Tyr Gly Arg Trp Tyr Phe Asp Val
1               5                   10

<210> SEQ ID NO 25
<211> LENGTH: 5
<212> TYPE: PRT
<213> ORGANISM: Mus musculus

<400> SEQUENCE: 25

Ser Ser Val Ser His
1               5

<210> SEQ ID NO 26
<211> LENGTH: 9
<212> TYPE: PRT
<213> ORGANISM: Mus musculus

<400> SEQUENCE: 26

Gln Gln Trp Ser Ser Thr Pro Arg Thr
1               5

<210> SEQ ID NO 27
<211> LENGTH: 106
<212> TYPE: PRT
<213> ORGANISM: Homo sapiens

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
```

```
                50              55              60
Tyr Ser Leu Ser Ser Thr Leu Thr Leu Ser Lys Ala Asp Tyr Glu Lys
 65              70              75              80

His Lys Val Tyr Ala Cys Glu Val Thr His Gln Gly Leu Ser Ser Pro
                85              90              95

Val Thr Lys Ser Phe Asn Arg Gly Glu Cys
            100             105

<210> SEQ ID NO 28
<211> LENGTH: 329
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
 1               5              10              15

Ser Thr Ser Gly Gly Thr Ala Ala Leu Gly Cys Leu Val Lys Asp Tyr
             20              25              30

Phe Pro Glu Pro Val Thr Val Ser Trp Asn Ser Gly Ala Leu Thr Ser
         35              40              45

Gly Val His Thr Phe Pro Ala Val Leu Gln Ser Ser Gly Leu Tyr Ser
     50              55              60

Leu Ser Ser Val Val Thr Val Pro Ser Ser Ser Leu Gly Thr Gln Thr
 65              70              75              80

Tyr Ile Cys Asn Val Asn His Lys Pro Ser Asn Thr Lys Val Asp Lys
                 85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320
```

Gln Lys Ser Leu Ser Leu Ser Pro Gly
            325

<210> SEQ ID NO 29
<211> LENGTH: 329
<212> TYPE: PRT
<213> ORGANISM: Artificial
<220> FEATURE:
<223> OTHER INFORMATION: variant heavy chain constant region (S239C)

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325